(12) United States Patent
Wilson et al.

(10) Patent No.: US 12,310,916 B2
(45) Date of Patent: May 27, 2025

(54) REAL-TIME METHODS TO ENABLE PRECISION-GUIDED CPR TO IMPROVE NEUROLOGICAL OUTCOME AND PREDICT BRAIN DAMAGE AFTER ISCHEMIC INJURY AND REPERFUSION

(71) Applicant: THE REGENTS OF THE UNIVERSITY OF CALIFORNIA, Oakland, CA (US)

(72) Inventors: Robert H. Wilson, Irvine, CA (US); Christian Crouzet, Irvine, CA (US); Yama Akbari, Irvine, CA (US); Bernard Choi, Irvine, CA (US); Bruce J. Tromberg, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 576 days.

(21) Appl. No.: 17/690,866

(22) Filed: Mar. 9, 2022

(65) Prior Publication Data
US 2022/0192919 A1  Jun. 23, 2022

Related U.S. Application Data

(63) Continuation-in-part of application No. 17/534,986, filed on Nov. 24, 2021, now abandoned, which is a
(Continued)

(51) Int. Cl.
*A61H 31/00* (2006.01)
*A61B 5/00* (2006.01)
(Continued)

(52) U.S. Cl.
CPC .......... *A61H 31/005* (2013.01); *A61B 5/0205* (2013.01); *A61B 5/0261* (2013.01);
(Continued)

(58) Field of Classification Search
CPC . A61B 5/0075; A61B 5/0086; A61B 5/02028; A61B 5/0205; A61B 5/0261;
(Continued)

(56) References Cited

U.S. PATENT DOCUMENTS 4,709,702 A   12/1987  Sherwin
D739,122 S     9/2015  Aimone et al.
(Continued)

FOREIGN PATENT DOCUMENTS

DE        10153360 A1     10/2001
WO    WO2008109699 A2    12/2008
(Continued)

OTHER PUBLICATIONS

Salvo et al. A 3D printed dry electrode for ECG/EEG recording, Sensors and Actuators A: Physical, Dec. 8, 2011, p. 96-102, Elsevie B.V.
(Continued)

*Primary Examiner* — Jonathan T Kuo
*Assistant Examiner* — Vynn V Huh
(74) *Attorney, Agent, or Firm* — NGUYEN TARBET IP LAW

(57) ABSTRACT

A multimodal optical imaging platform is used to obtain cerebral perfusion-metabolism mismatch metrics for rapid assessment of acute brain injury, ongoing (real-time) feedback to optimize cardiopulmonary resuscitation to improve neurological outcome, and rapid prognosis of recovery. Light of several wavelengths and types is delivered to the tissue, which is then absorbed and scattered by tissue components such as blood and cellular components. Some of this light scatters back to the surface, where it is captured by a detector. The resulting data are processed to obtain blood flow and oxygenation parameters, as well as tissue scattering. These parameters are then combined to calculate
(Continued)

metabolism and flow-metabolism coupling/decoupling metrics, which are used to determine ischemic damage, ongoing need for optimal blood flow and oxygenation, and to predict cerebral recovery in patients with acute brain injury during and immediately after cardiac arrest, stroke, traumatic brain injury, etc.

**7 Claims, 17 Drawing Sheets
(16 of 17 Drawing Sheet(s) Filed in Color)**

Related U.S. Application Data continuation-in-part of application No. 17/377,123, filed on Jul. 15, 2021, and a continuation-in-part of application No. 17/277,616, filed on Mar. 18, 2021, and a continuation-in-part of application No. PCT/US2020/053144, filed on Sep. 28, 2020, said application No. 17/377,123 is a continuation-in-part of application No. 16/985,113, filed on Aug. 4, 2020, now abandoned, said application No. 17/534,986 is a continuation-in-part of application No. PCT/US2020/035440, filed on May 29, 2020, said application No. 16/985,113 is a continuation-in-part of application No. PCT/US2020/035440, filed on May 29, 2020, and a continuation-in-part of application No. 16/837,478, filed as application No. PCT/US2019/052486 on Sep. 23, 2019, now abandoned.

(60) Provisional application No. 63/032,491, filed on May 29, 2020, provisional application No. 62/907,595, filed on Sep. 28, 2019, provisional application No. 62/854,215, filed on May 29, 2019, provisional application No. 62/827,668, filed on Apr. 1, 2019, provisional application No. 62/734,417, filed on Sep. 21, 2018.

(51) Int. Cl.
| | | |
|---|---|---|
| *A61B 5/02* | (2006.01) | |
| *A61B 5/0205* | (2006.01) | |
| *A61B 5/026* | (2006.01) | |
| *A61B 5/145* | (2006.01) | |
| *A61B 5/1455* | (2006.01) | |
| *A61B 5/369* | (2021.01) | |
| *A61N 1/39* | (2006.01) | |

(52) U.S. Cl.
CPC ...... *A61B 5/14552* (2013.01); *A61B 5/14553* (2013.01); *A61B 5/369* (2021.01); *A61H 2230/207* (2013.01); *A61N 1/39044* (2017.08)

(58) Field of Classification Search
CPC ............ A61B 5/14542; A61B 5/14546; A61B 5/14552; A61B 5/14553; A61B 5/369; A61B 5/4836; A61B 5/4866; A61B 5/4875; A61B 5/6814; A61B 5/6841; A61H 2230/207; A61H 2230/25; A61H 31/005; A61N 1/39044
See application file for complete search history.

(56) References Cited

U.S. PATENT DOCUMENTS

| | | |
|---|---|---|
| 9,730,649 B1 | 8/2017 | Jepsen |
| 10,009,644 B2 | 6/2018 | Aimone et al. |
| 10,321,842 B2 | 6/2019 | Garten et al. |
| 2004/0068199 A1 | 4/2004 | Echauz et al. |
| 2005/0143589 A1 | 6/2005 | Donoghue et al. |
| 2006/0281983 A1 | 12/2006 | Al-Ali et al. |
| 2007/0191689 A1 | 8/2007 | Elitok |
| 2008/0177572 A1 | 7/2008 | Fuhrman et al. |
| 2009/0118622 A1 | 5/2009 | Durkin et al. |
| 2010/0241100 A1 | 9/2010 | Blumenfeld et al. |
| 2011/0105912 A1* | 5/2011 | Widman ............... A61B 5/4076 600/483 |
| 2012/0143020 A1 | 6/2012 | Bordoley et al. |
| 2013/0261183 A1 | 10/2013 | Bhagat |
| 2014/0018649 A1 | 1/2014 | Jespersen et al. |
| 2014/0088996 A1 | 3/2014 | Damani |
| 2015/0051521 A1 | 2/2015 | Woerlee et al. |
| 2015/0257674 A1 | 9/2015 | Jordan et al. |
| 2016/0317385 A1 | 11/2016 | Salcido et al. |
| 2016/0345880 A1 | 12/2016 | Nakaji et al. |
| 2017/0135594 A1 | 5/2017 | Hartings et al. |
| 2018/0044278 A1 | 2/2018 | Bazan et al. |
| 2018/0085047 A1 | 3/2018 | Hartings et al. |
| 2018/0103861 A1* | 4/2018 | Sutin ..................... A61B 5/318 |
| 2018/0246570 A1 | 8/2018 | Coleman et al. |
| 2018/0308390 A1 | 10/2018 | Moser et al. |
| 2019/0053721 A1 | 2/2019 | Boas et al. |
| 2019/0113973 A1 | 4/2019 | Coleman et al. |
| 2019/0117500 A1 | 4/2019 | Shaw et al. |
| 2019/0159675 A1 | 5/2019 | Sengupta et al. |
| 2019/0306438 A1 | 10/2019 | Regan et al. |
| 2019/0306439 A1 | 10/2019 | Morales Delgado et al. |
| 2019/0384392 A1 | 12/2019 | Aimone et al. |
| 2020/0019243 A1 | 1/2020 | Aimone et al. |

FOREIGN PATENT DOCUMENTS

| | | |
|---|---|---|
| WO | WO2016164891 A1 | 10/2016 |
| WO | 2020243658 A1 | 12/2020 |

OTHER PUBLICATIONS

Wiebe et al. EEG-PEN for Medical Emergencies, Biomedical Engineering / Biomedizinische Technik Oct. 23, 2009, vol. 47, Issue s1a, DOI: https://doi.org/10.1515/bmte.2002.47.s1a.308.

Krachunov et al. 3D Printed Dry Electrodes, Sensors Journal, 1635, pp. 1-18, Oct. 2, 2016 doi:10.3390/s16101635.

Cuccia et al. "Quantitation and mapping of tissue optical properties using modulated imaging." Journal of biomedical optics 14.2 (2009): 024012.

Dreier et al. "Spreading depolarization is not an epiphenomenon but the principal mechanism of the cytotoxic edema in various gray matter structures of the brain during stroke." Neuropharmacology 134 (2018): 189-207.

* cited by examiner

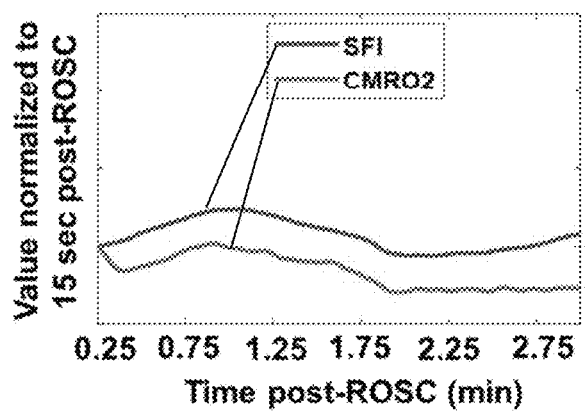
FIG. 6A Short CA
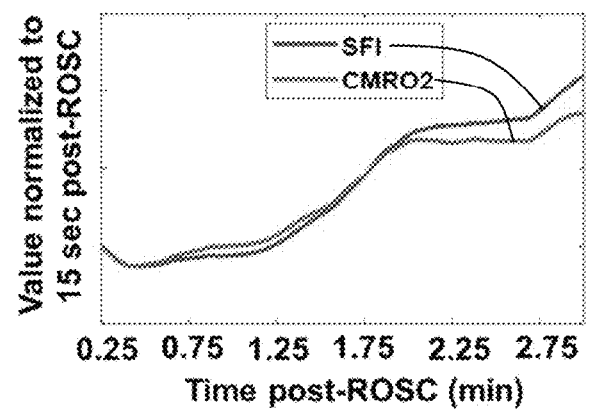
FIG. 6B Prolonged CA
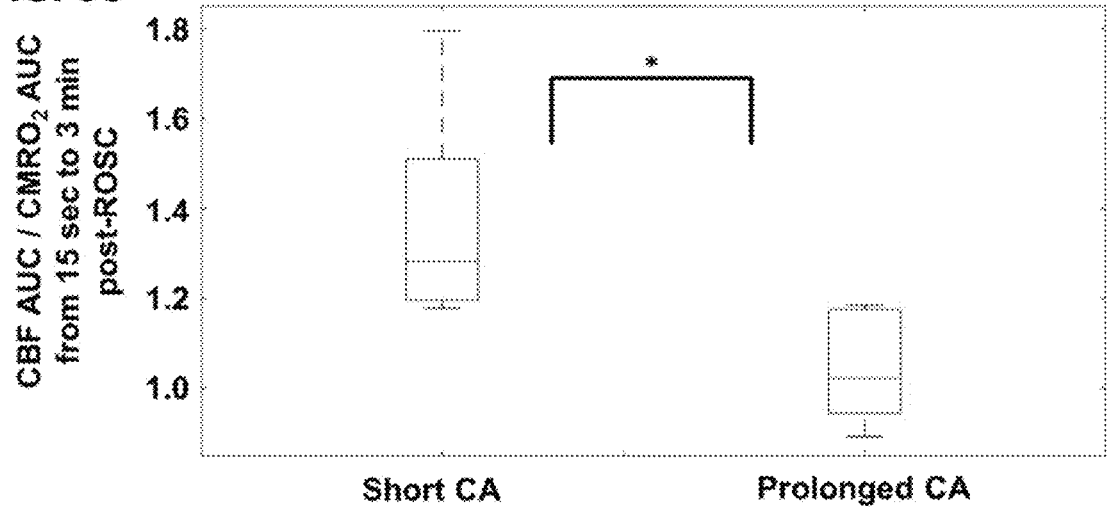
FIG. 6C
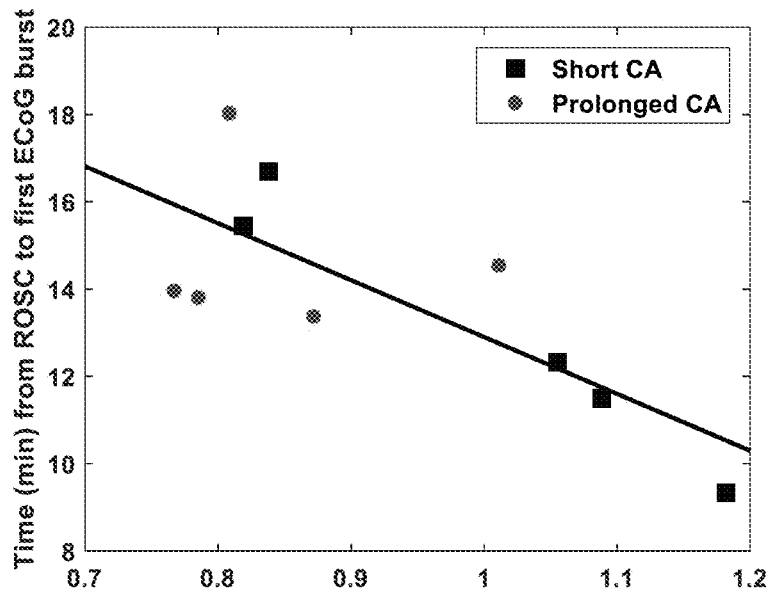
FIG. 7

(1) Correcting Speckle Contrast for Tissue Absorption and Scattering (2) Calculating Absolute Cerebral Metabolic Rate of Oxygen ($CMRO_2$)

$$CMRO_2 = 4\alpha(v_c)(ctHb_v)(Hb_M/\langle ctHb_{tot}\rangle_\rho)$$

Ratio of hemoglobin concentration in blood to measured hemoglobin concentration in tissue (needed to correct for partial volume effect)

Tissue concentration of deoxy-hemoglobin in region of interest above large vein from SFDI data Flow speed from LSI data corrected for tissue absorption and scattering To solve for $\alpha$, we use a zero-flow boundary condition:

$$4\alpha(v_c)|_{t \to t_{asph^-}}(ctHb_v)|_{t \to t_{asph^-}} = 4(dctHb_v/dt)|_{t \to t_{asph^+}}$$

Flow speed right before start of asphyxia

Tissue deoxy-hemoglobin concentration in region of interest above large vein, from SFDI data, right before start of asphyxia Rate of change of tissue deoxy-hemoglobin concentration in region of interest above large vein, from SFDI data, during time period spanning <1 min immediately following start of asphyxia Revised from Ghijsen, et al. J. Biomed. Opt. 23, 036013 (2018)

FIG. 12

$CMRO_2$ = moles of oxygen consumed by the tissue per unit time $ctHb$ = moles of hemoglobin that had its oxygen consumed by the tissue per unit volume → $\boxed{CMRO_2 = ctHb * \text{(volume of tissue being oxygenated per unit time)}}$ How do we calculate the volume of tissue that is being oxygenated per unit time?

- One approach is to say that the diffusion coefficient $D_B$ represents the area of tissue being oxygenated (via blood flow) per unit time.

- Multiplying the area of tissue being oxygenated by the mean penetration depth of the light in the tissue gives an estimate of the optically-measured volume of tissue being oxygenated (via blood flow) per unit time.

- Then, our final equation for absolute $CMRO_2$ can be written as:

→ $\boxed{CMRO_2 = (ctHb)*(D_B)*(\delta)}$   (best to use $ctHb$ in venous ROI)

where $D_B$ is the absorption- and scatter-corrected diffusion coefficient and $\delta$ is derived from diffusion theory using the measured $\mu_a$ and $\mu_s'$

FIG. 14

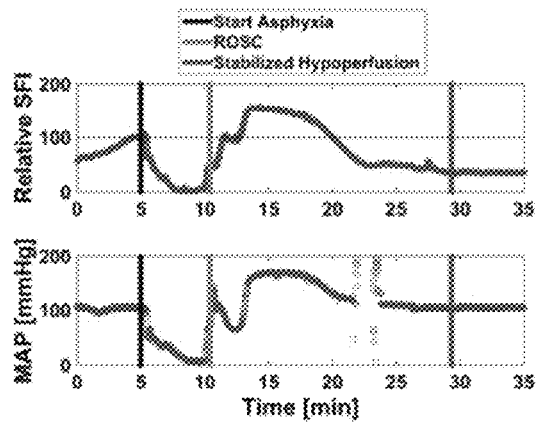
FIG. 17A
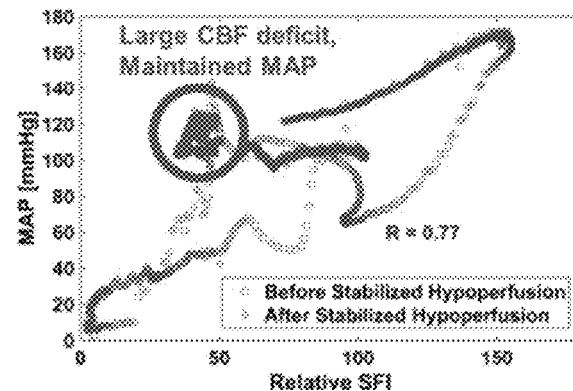
FIG. 17B
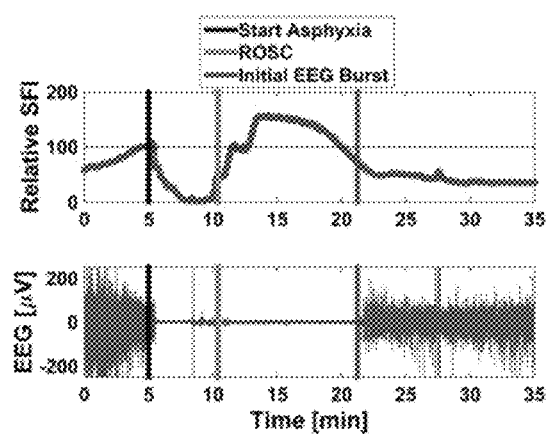
FIG. 18A
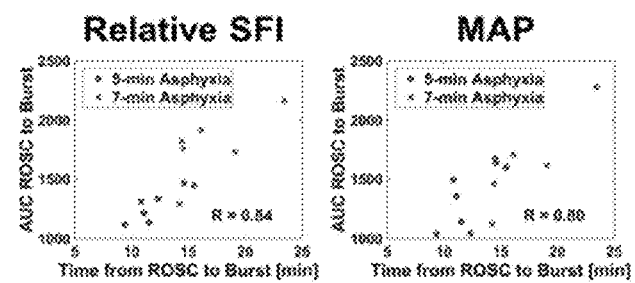
FIG. 18B    FIG. 18C
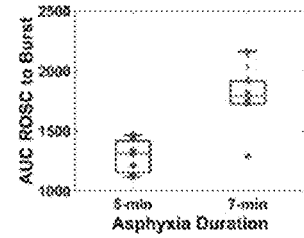
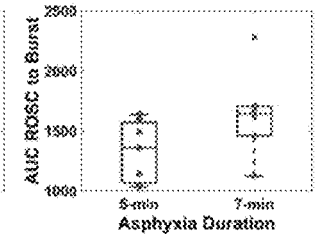
FIG. 18D    FIG. 18E
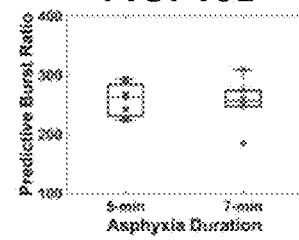
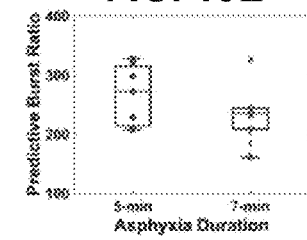
FIG. 18F    FIG. 18G

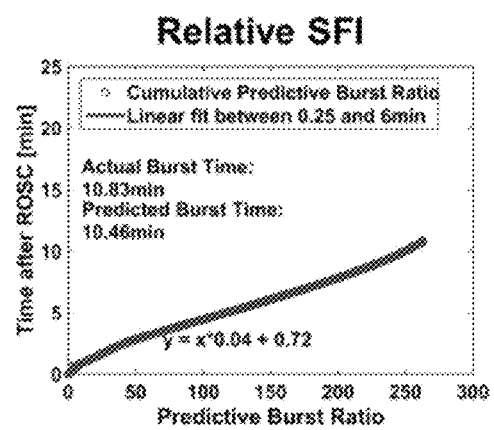
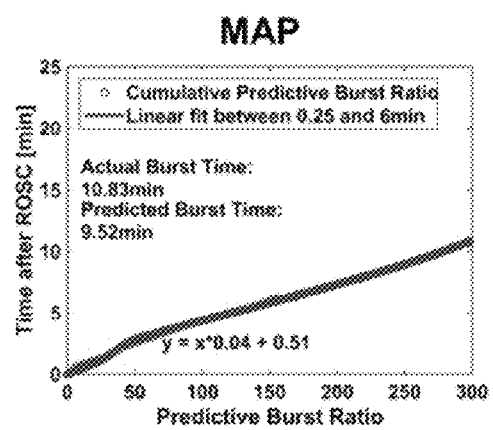
FIG. 19A    FIG. 19B
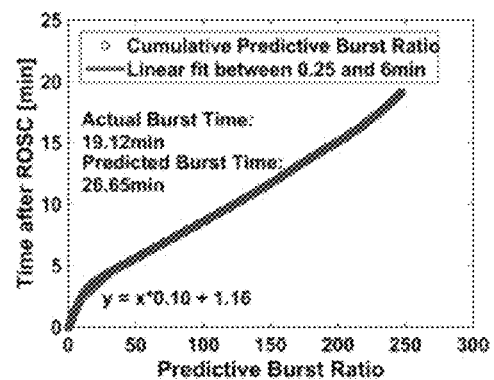
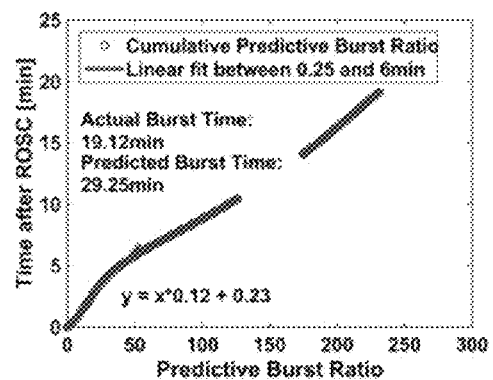
FIG. 19C    FIG. 19D

REAL-TIME METHODS TO ENABLE PRECISION-GUIDED CPR TO IMPROVE NEUROLOGICAL OUTCOME AND PREDICT BRAIN DAMAGE AFTER ISCHEMIC INJURY AND REPERFUSION

CROSS-REFERENCES TO RELATED APPLICATIONS

This application is a continuation-in-part and claims benefit of U.S. patent application Ser. No. 17/534,986 filed Nov. 24, 2021, the specification of which is incorporated herein in its entirety by reference.

U.S. patent application Ser. No. 17/534,986 is a continuation-in-part and claims benefit of PCT Application No. PCT/US2020/035440 filed May 29, 2020, which claims benefit of U.S. Provisional Application No. 62/854,215, filed May 29, 2019, the specification(s) of which is/are incorporated herein in their entirety by reference.

U.S. patent application Ser. No. 17/534,986 is also a continuation-in-part and claims benefit of U.S. patent application Ser. No. 17/377,123 filed Jul. 15, 2021, which is continuation-in-part and claims benefit of U.S. patent application Ser. No. 16/985,113 filed Aug. 4, 2020, now abandoned, which is a continuation-in-part and claims benefit of U.S. patent application Ser. No. 16/837,478 filed Apr. 1, 2020, now abandoned, which is a non-provisional and claims benefit of U.S. Provisional Application No. 62/827,668 filed Apr. 1, 2019, the specification(s) of which is/are incorporated herein in their entirety by reference.

Also, U.S. patent application Ser. No. 16/985,113 is a non-provisional and claims benefit of U.S. Provisional Application No. 63/032,491 filed May 29, 2020, the specification(s) of which is/are incorporated herein in their entirety by reference.

Further, U.S. patent application Ser. No. 16/985,113 is a continuation-in-part and claims benefit of PCT Application No. PCT/US2020/035440 filed May 29, 2020, which claims benefit of U.S. Provisional Application No. 62/854,215 filed May 29, 2019, the specification(s) of which is/are incorporated herein in their entirety by reference.

U.S. patent application Ser. No. 17/534,986 is also a continuation-in-part and claims benefit of PCT Application No. PCT/US2020/053144 filed Sep. 28, 2020, which claims benefit of U.S. Provisional 62/907,595 filed Sep. 28, 2019, the specification(s) of which is/are incorporated herein in their entirety by reference.

U.S. patent application Ser. No. 17/534,986 is also a continuation-in-part and claims benefit of U.S. patent application Ser. No. 17/277,616 filed Mar. 18, 2021, which is a 371 and claims benefit of PCT Application No. PCT/US2019/052486 filed Sep. 23, 2019, which claims benefit of U.S. Provisional Application No. 62/734,417 filed Sep. 21, 2018, the specification(s) of which is/are incorporated herein in their entirety by reference.

STATEMENT REGARDING FEDERALLY SPONSORED RESEARCH OR DEVELOPMENT

This invention was made with government support under Grant Nos. R21 EB024793, P41 EB015890, KL2 TR000147, and TL1 TR001415 awarded by the National Institutes of Health, and DGE-1321846 awarded by the National Science Foundation. The government has certain rights in the invention.

BACKGROUND OF THE INVENTION

Field of the Invention

The present invention relates to medical devices and methods for rapidly assessing ischemic brain damage and prognosing neurological recovery during onset of injury, during intervention (e.g., during resuscitation), or immediately after reperfusion.

Background Art

Cardiac arrest (CA) afflicts over 565,000 people annually in the United States. Survivors of CA typically sustain significant brain damage due to cerebral ischemia, reperfusion injury, and compromised cerebral autoregulation. To improve patient outcomes, it is essential to better understand the complex response of the brain to CA and cardiopulmonary resuscitation (CPR). Specifically, it is crucial to quantitatively monitor the relationship between cerebral blood flow (CBF) and brain metabolism following CPR. After hypoxic-ischemic injury (e.g., CA), reperfusion (e.g., CPR) can deliver oxygenated blood to the brain to support energy production, but this massive influx of oxygen can also cause neuronal injury if it is not metabolized efficiently. As a result, relying on only perfusion data is insufficient to accurately assess the hemodynamic response of CA patients, and a complementary measure of cerebral metabolism is required for correct assessment of injury severity and prognostication of recovery. By monitoring CBF and brain metabolism in tandem, mismatches between these two quantities can be identified and corrected to improve patient outcome. This is particularly critical during the initial minutes (or even seconds) of CPR as well as the subsequent seconds, minutes, and hours after the conclusion of CPR, when the most rapid hemodynamic changes occur and interventions targeting CBF are likely to be most effective.

Early intervention is critical for improving outcome for patients suffering cerebral ischemia, but there are no reliable quantitative methods for rapidly diagnosing severity of injury, prognosing outcome, and informing treatment in real time. The prior art typically uses either cerebral perfusion or oximetry, or it may rely on peripheral blood pressure/oxygenation. For instance, hemodynamic status is typically monitored in emergency and intensive care settings by measuring blood pressure and blood gas concentration from the radial or femoral artery. However, these measurements occur distant from the brain and are often not informative of cerebral hemodynamic processes. Thus, the prior art attempts to quantify cerebral perfusion and metabolism struggle to do so sufficiently and quickly enough to enable the clinician to take early action.

Further still, methods for direct measurement of oxygen consumption in the brain are typically invasive and do not provide any information about perfusion. Techniques for non-invasive CBF measurement do not have the temporal resolution required to monitor rapid changes in cerebral perfusion and metabolism. As such, it remains difficult to obtain accurate real-time feedback on CBF and metabolism concurrently to guide emergent clinical intervention to optimize neurological outcome for CA patients. Therefore, early diagnosis/prognosis/guided treatment for cerebral ischemia is a currently unmet clinical need.

BRIEF SUMMARY OF THE INVENTION

It is an objective of the present invention to provide a multimodal optical imaging platform and method for measuring of cerebral blood flow (CBF), brain tissue oxygenation ($StO_2$), cerebral metabolic rate of oxygen ($CMRO_2$), and cerebral electrical activity (electrocorticography; ECoG), as specified in the independent claims. Embodiments of the invention are given in the dependent claims. Embodiments of the present invention can be freely combined with each other if they are not mutually exclusive.

In some aspects, the present invention provides near-continuous measurements to enable assessment of rapid dynamic changes that may be critical for improved diagnosis and prognosis. These changes may be measured as rapidly as within the first minute of resuscitation and can continue to the post-resuscitation period. The present invention incorporates perfusion and oximetry together to quantify cerebral metabolism and flow-metabolism coupling/decoupling at specific time windows after ischemia and reperfusion, which serve as a critical, unique distinction as cerebral ischemia can lead to autonomic dysregulation, not just deficits in perfusion or oxygenation individually. Also, while many existing techniques are invasive and/or use exogenous contrast agents, the present invention, in contrast, is a minimally-invasive approach that relies on optical signals from the body. In some manifestations, this technology may involve completely non-contact optical imaging approaches to monitor the brain. In other manifestations, this technology may involve fiber-optic probes that make contact with the skin surface to non-invasively measure changes in the underlying brain tissue. In addition to cardiac arrest, there are many different clinical scenarios in which the present invention can be used for rapid detection and characterization of cerebral ischemia critical for helping improve patient outcome. These applications include, but are not limited to: focal stroke, intracerebral hemorrhage, subarachnoid hemorrhage, traumatic brain injury, sleep apnea, and drug overdose.

In some embodiments, the invention includes methods that calculate values of key parameters related to blood flow, oxygen consumption, tissue scattering, cytotoxic and vasogenic edema, perfusion/metabolism coupling/uncoupling, neurovascular coupling/uncoupling, and autonomic regulation in the brain following ischemia and reperfusion. These parameters can be used to diagnose the severity/duration of ischemia and prognose cerebral recovery.

In some manifestations, the invention may also be used in conjunction with different modalities of neural stimulation, in cases where such stimuli are employed to drive reperfusion, enhance cerebral recovery, and/or test autoregulation. In these manifestations, the invention may be used to quantitatively characterize the brain's response to the neural stimulus, the brain's degree of autoregulation, and/or the effectiveness of the stimulation technique.

One of the unique and inventive technical features of the present invention is that it provides continuously-updating, quantitative metrics of brain dysfunction by using cerebral blood flow and metabolism parameters together. Without wishing to limit the invention to any theory or mechanism, this feature is important because the autoregulation of the brain is disrupted during ischemia so these parameters may be critical for improved diagnosis and prognosis, and may be further used to inform treatment. Preliminary preclinical studies show that the present invention may have diagnostic and prognostic potential in the very early phases (e.g., within the first minute) of ischemia and reperfusion. For instance, multiple phases of cerebral hemodynamic recovery, with different degrees of mismatch between CBF and $CMRO_2$, were observed following CPR. It was further observed that within 1 min post-resuscitation, $CBF/CMRO_2$ is indicative of CA duration/severity and prognostic (with 87% accuracy) of short-term neurological recovery measured by the initiation of ECoG activity (e.g. the time that ECoG activity resumes). These measurements provide the earliest known metrics for assessment of CA severity and prognosis following resuscitation from CA. Importantly, they do not require pre-resuscitation data, making them potentially translational for intensive care and emergency-response settings in which pre-CA information is unavailable. In addition, these metrics may enable real-time feedback during potentially critical dynamic time points immediately after resuscitation to inform treatment for CA patients. None of the presently known prior references or work has the unique inventive technical feature of the present invention.

Furthermore, the prior arts teach away from the present invention. For example, after a patient is resuscitated, medical personnel having ordinary skill in the art would typically monitor a patient's blood pressure at his or her peripheries. Since the patient's EEG often shows no significant electrical activity in the brain in the first few minutes after resuscitation, the medical personnel would neither consider nor have any motivation to monitor the cerebral blood flow or metabolism during this period. In contrast, the present invention monitors both cerebral blood flow and metabolism immediately after resuscitation, which is counterintuitive to popular belief. As a result, the present invention has surprisingly found that by monitoring CBF and $CMRO_2$, a metric can be calculated that can provide information about the severity of brain damage. Furthermore, when this metric is obtained during a critical window after resuscitation, it has a higher accuracy that allows for early prognosis and prescribing of proper treatment to improve the patient's recovery.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

LIST OF ABBREVIATIONS

CA—cardiac arrest
CPR—cardiopulmonary resuscitation
CBF—cerebral blood flow
LSI—laser speckle imaging
ROI—region of interest
SFI—speckle flow index
$CMRO_2$—cerebral metabolic rate of oxygen
ECoG—electrocorticography
ROSC—return of spontaneous circulation
sCMOS—scientific complementary metal-oxide semiconductor
SFDI—spatial frequency domain imaging

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which:

FIG. 1A is a non-limiting flow diagram embodiment according to a method of the present invention.

FIG. 1B shows an experimental set-up of the present invention comprising instrumentation for high-speed LSI and SFDI. Spatially-modulated LEDs and a sCMOS camera were used for SFDI. An 809 nm laser and 60 fps camera were used for LSI. The rapid LSI and SFDI system was integrated into an "animal intensive care unit" setup for monitoring the response of the brain to CA and CPR in a preclinical rat model. A craniectomy was performed to expose a ~6 mm×4 mm region of the brain for imaging, and four ECoG electrodes were implanted for monitoring cerebral electrical activity.

FIG. 1C shows representative maps of CBF and brain oxygenation in a CA/CPR experiment. Notable differences in CBF and oxygenation ($StO_2$) were imaged during four phases: baseline, CA, hyperemic response to CPR, and post-hyperemic hypoperfusion. At baseline, normal cerebral perfusion and oxygenation were observed. During CA, blood flow was completely absent from the brain and cerebral oxygenation dropped rapidly, indicative of oxygen consumption. During post-ROSC hyperemia, states of hyper-perfusion and hyper-oxygenation were observed. During hypoperfusion, CBF stabilized at a level below baseline, yet increased metabolic activity was observed, reflected by a reduction in oxygenation.

FIG. 2 shows different phases of CBF and metabolism observed during isoflurane washout and subsequent onset of CA. (a) CBF (green), oxy-hemoglobin concentration ($ctHbO_2$, red), deoxy-hemoglobin concentration (ctHb, blue), and $CMRO_2$ (magenta), averaged over a region of interest for the same rat as in FIG. 1B during baseline (Phase I) and CA (Phase II). Note the rise in $CMRO_2$ was slightly higher than the rise in CBF during washout, and this becomes much more dramatic during the initial seconds after asphyxia, suggesting flow/metabolism decoupling. (b) The ECoG signal was robust during Phase I, but reached pulseless electrical activity within ~30 sec after onset of asphyxia (Phase II). (c) Mean arterial pressure decreased sharply at the same time as onset of pulseless electrical activity.

FIG. 3 shows CBF (green), oxy-hemoglobin concentration ($ctHbO_2$, red), deoxy-hemoglobin (ctHb, blue), and $rCMRO_2$ (magenta), averaged over a region of interest for the same rat as in FIG. 2, during CPR (orange shaded window), hyperemia (Phase III), and hypoperfusion (Phase IV). In addition, the associated whole-band ECoG signal and mean arterial pressure are shown. Soon after a decrease in CBF following hyperemia, ECoG bursting resumed and deoxy-hemoglobin increased, with oxygen extraction linked to the increased neuronal activity. Note that these hemodynamic changes observed during phases III and IV are not reflected in the waveform of mean arterial pressure, suggesting a decoupling between cerebral and peripheral hemodynamics. Multiple phases of cerebral flow-metabolism coupling and uncoupling occurred during Phase III. Flow-metabolism coupling (denoted as "coupling" in the figure) is defined as a period of concomitant changes in CBF and $CMRO_2$ with similar slopes. Flow-metabolism uncoupling (denoted as "uncoupling" in the figure) is defined as a period during which CBF and $CMRO_2$ have opposite slopes or one has a nonzero slope and the other has roughly zero slope.

Figure 5A:
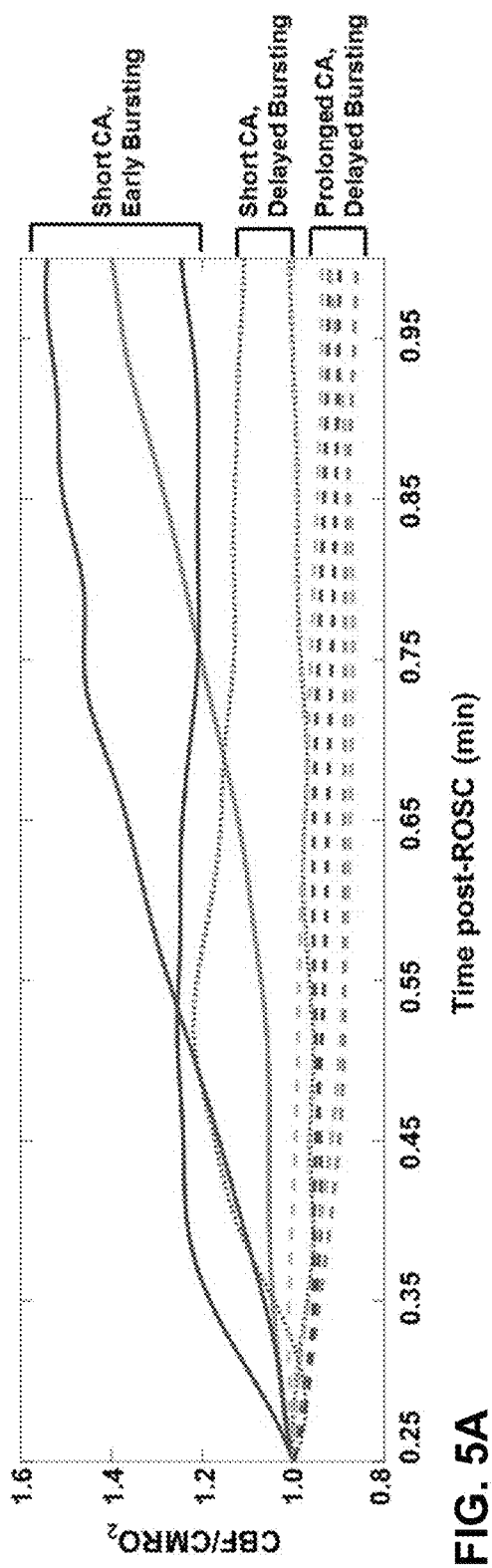
Figure 5B:
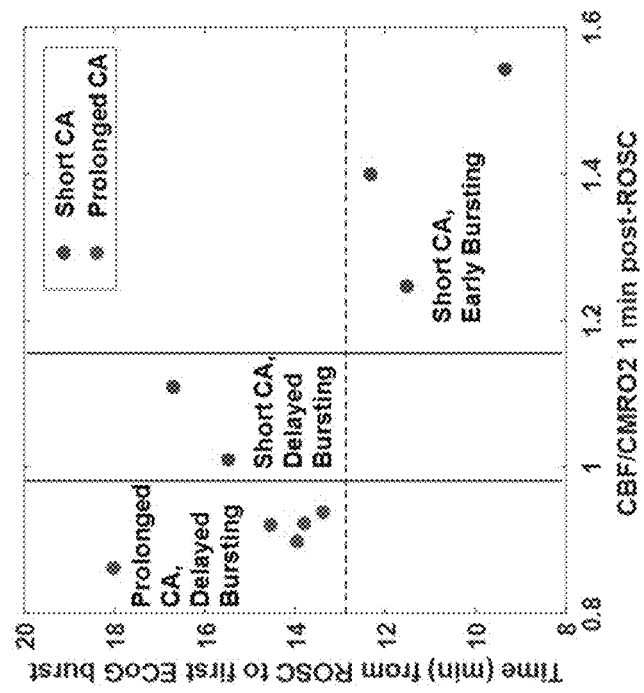

FIGS. 5A-5B show a $CBF/CMRO_2$ ratio during the first minute after resuscitation for 5 rats with shorter CA (5 min asphyxia; solid lines) and 5 rats with prolonged CA (7 min asphyxia; dashed lines). The ratio of $CBF/CMRO_2$ (normalized to 15 sec post-ROSC) can be used to retrospectively determine severity of CA and simultaneously provide a preliminary prediction of expected outcome. This ratio does not require any pre-ROSC information, making it well-suited for potential translation to emergency response and intensive care settings. In FIG. 5A, using $CBF/CMRO_2$ values, the time window of ~0.5-2 min post-ROSC is the most useful for CA severity assessment and prognosis. For instance, at 1 min post-ROSC, a clear separation is observed between rats that had prolonged CA (7 min asphyxia) and rats that had shorter CA (5 min asphyxia). Rats that had short CA but ended up experiencing delayed ECoG bursting have $CBF/CMRO_2$ values that fall above those of the rats with prolonged CA but below the other rats with shorter CA. In FIG. 5B, a threshold of $CBF/CMRO_2 = 1$ (dashed vertical line), suggestive of paired flow/metabolism coupling, can completely distinguish rats that had shorter duration of CA (5 min asphyxia) from prolonged CA duration (7 min asphyxia). A second threshold of $CBF/CMRO_2 \sim 1.2$ completely distinguished rats that had good short-term cerebral electrical recovery (earlier ECoG bursting) from rats that had poor short-term cerebral electrical recovery (later ECoG bursting), regardless of CA duration. These correlations vanish within the first 3 min post-ROSC, suggesting the presence of a transient ultra-early window for assessing CA severity and predicting neurological recovery.

FIGS. 6A and 6B show CBF and $CMRO_2$, normalized to the corresponding value at 15 sec post-ROSC, for the first 5 min post-ROSC for representative rats with shorter CA and longer CA, respectively. CBF exceeds $CMRO_2$ during first 5 min post-ROSC for a representative rat with short (5 min) CA, but not for prolonged (7 min) CA.

FIG. 6C shows that the ratio of the areas under the CBF and $CMRO_2$ curves (AUC). The ratio of the areas from 15 sec-3 min post-ROSC is significant (*, p<0.02 from Wilcoxon rank-sum test) for distinguishing rats that underwent short CA from those with prolonged CA. Prior to the AUC calculation, the CBF and CMRO2 were normalized to their values at 15 sec post-ROSC. No pre-ROSC information was required for this calculation.

FIG. 7 shows CBF, measured at 30 sec post-ROSC and normalized to its value at 15 sec post-ROSC. The CBF is linearly related to ECoG burst time (black line; R=−0.77, p=0.01 from Pearson correlation). Using a linear regression model with a leave-one-out cross-validation algorithm, CBF at 30 sec post-ROSC predicted first ECoG burst to within 16% over the full cohort of rats in the study (5 min and 7 min asphyxia times). No pre-ROSC information was required for this calculation. This correlation vanished within 2 min after ROSC.

Figure 8:
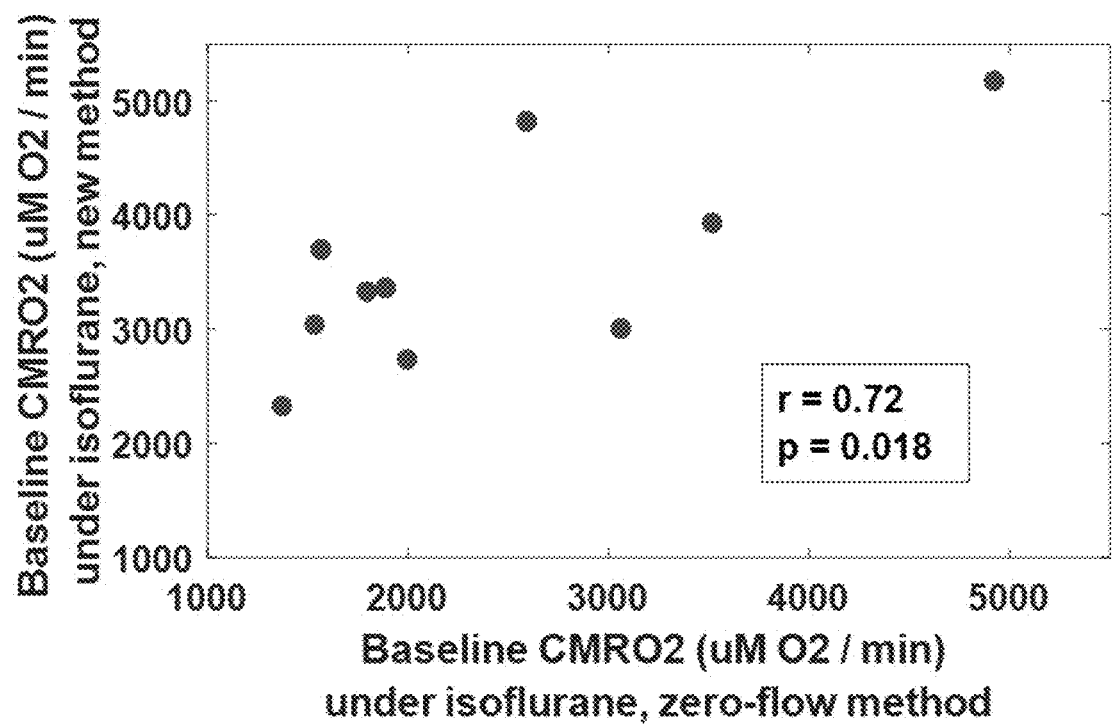

FIG. 8 shows a plot which illustrates that CMRO2 values measured in anesthetized rats without need for a physiological perturbation correlate well with values measured using the previous "zero-flow" perturbation method. This result demonstrates an additional embodiment of the invention whereby measurements of CMRO2 in absolute physiological units can be obtained rapidly for any state of the subject (e.g., baseline, during injury, during intervention, during recovery) without need for measurement of the other states or need for performing a dynamic maneuver to perturb the physiology of the subject. This allows for longitudinal comparison between subjects and a given subject at multiple discrete time points separated by hours, days, months, or even years, using the perturbation-free metric of absolute CMRO2 described here.

Figure 9:
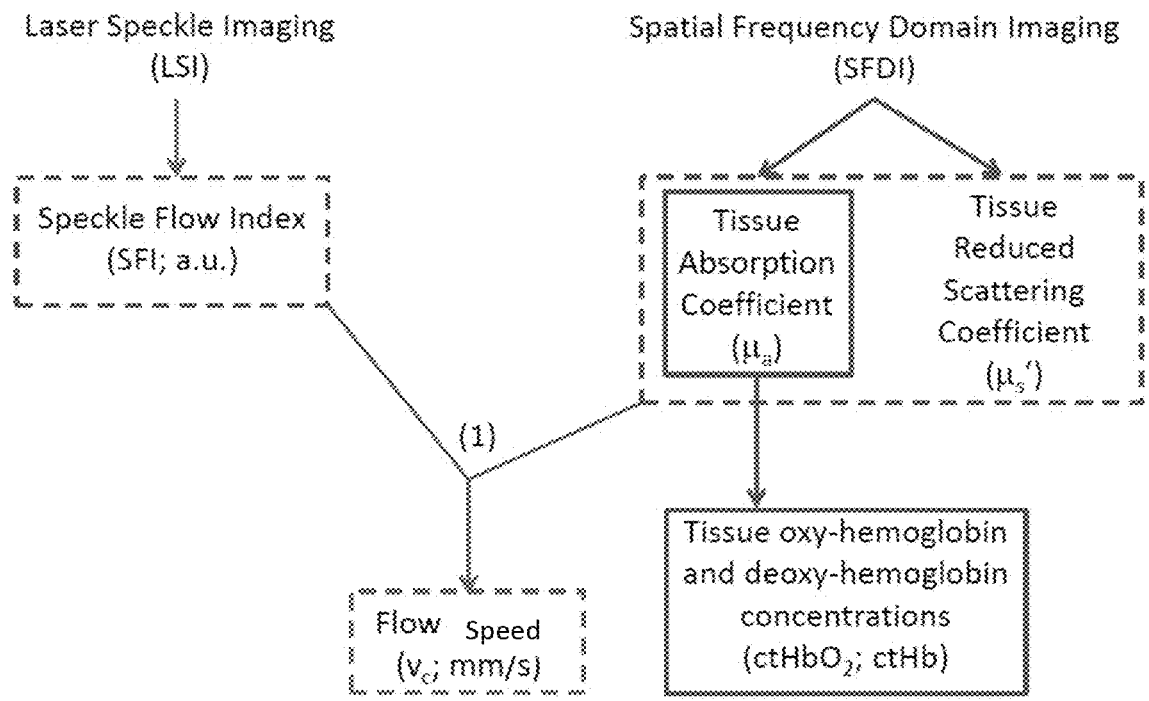

FIG. 9 shows an embodiment where cerebral blood flow data (speckle flow index; SFI) from laser speckle imaging (LSI) is combined with tissue absorption and scattering data (absorption coefficient mua, reduced scattering coefficient mus') from spatial frequency domain imaging (SFDI) to correct the SFI measurement for the effect of absorption and scattering and fit for a blood flow parameter in absolute physiological units. In some embodiments (as in this example), the parameter is directed flow speed $v_c$ (units of mm/s). In other embodiments, the parameter is Brownian diffusion coefficient $D_b$ (units of mm$^2$/s).

Figures 10, 11:
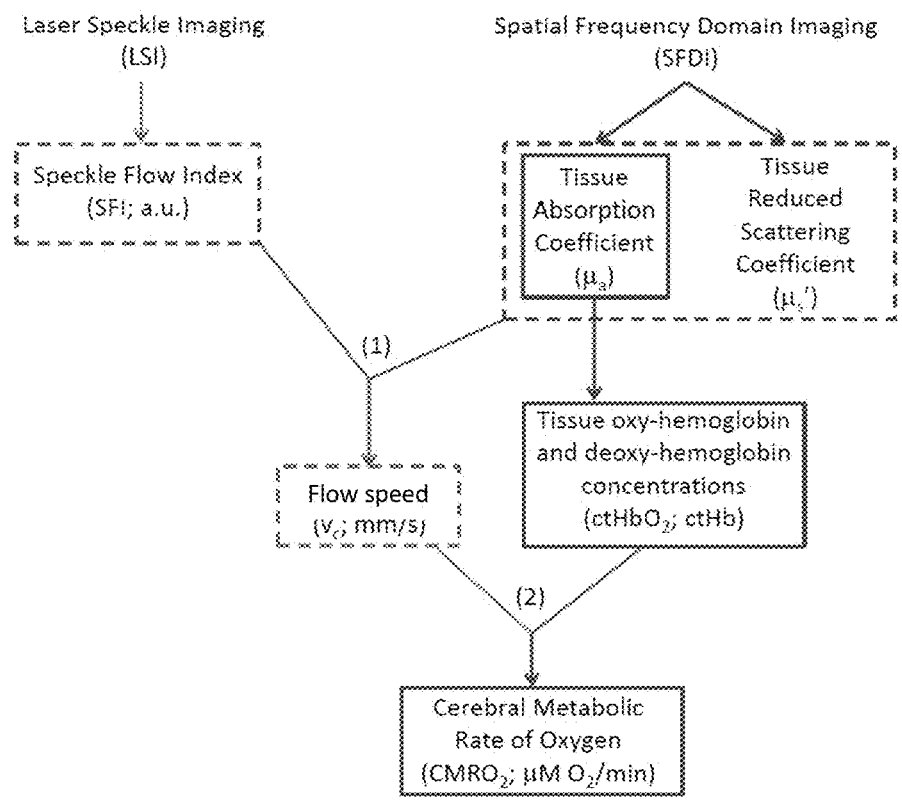

FIG. 10 shows an embodiment where the displayed equation is used to perform the fitting procedure to extract the blood flow parameter (e.g., $v_c$ or $D_b$) in absolute physiological units. In the equation, the variable K is the measured speckle contrast obtained from LSI, and the variable G1 is a function of the blood flow parameter (e.g., $v_c$ or $D_b$) and the tissue absorption and scattering coefficients measured with SFDI. Note: The equation may be solved for Brownian diffusion coeff $D_B$, directed-flow term $v_c$, or both.

FIG. 11 shows an embodiment where the blood flow parameter (e.g., $v_c$ or $D_b$) is combined with the tissue oxy-hemoglobin and deoxy-hemoglobin concentrations measured with SFDI to calculate the cerebral metabolic rate of oxygen (CMRO$_2$) in absolute physiological units (e.g., uM O$_2$/min).

FIG. 12 (top equation) shows an embodiment where the top equation is used to calculate the absolute CMRO$_2$ using blood flow and hemoglobin parameters multiplied by a coefficient (alpha). Slide 17 (bottom equation) shows how the (alpha) coefficient is determined by using a "zero-flow" boundary condition (e.g., start of asphyxia in cardiac arrest preclinical experiments), where blood flow is temporarily stopped and the metabolism of oxygen during this "zero-flow" state is attributed completely to the rate of change of deoxy-hemoglobin in the tissue. The CMRO$_2$ expression shortly before this "zero-flow" condition is initiated (left hand side of equation) is set equal to the CMRO$_2$ expression shortly after this "zero-flow" condition is initiated (right hand expression). This boundary condition equation is then solved to obtain the value of the coefficient (alpha), which is inserted back into the top equation to calculate the CMRO$_2$ in absolute physiological units (e.g., uM O$_2$/min).

Figure 13:
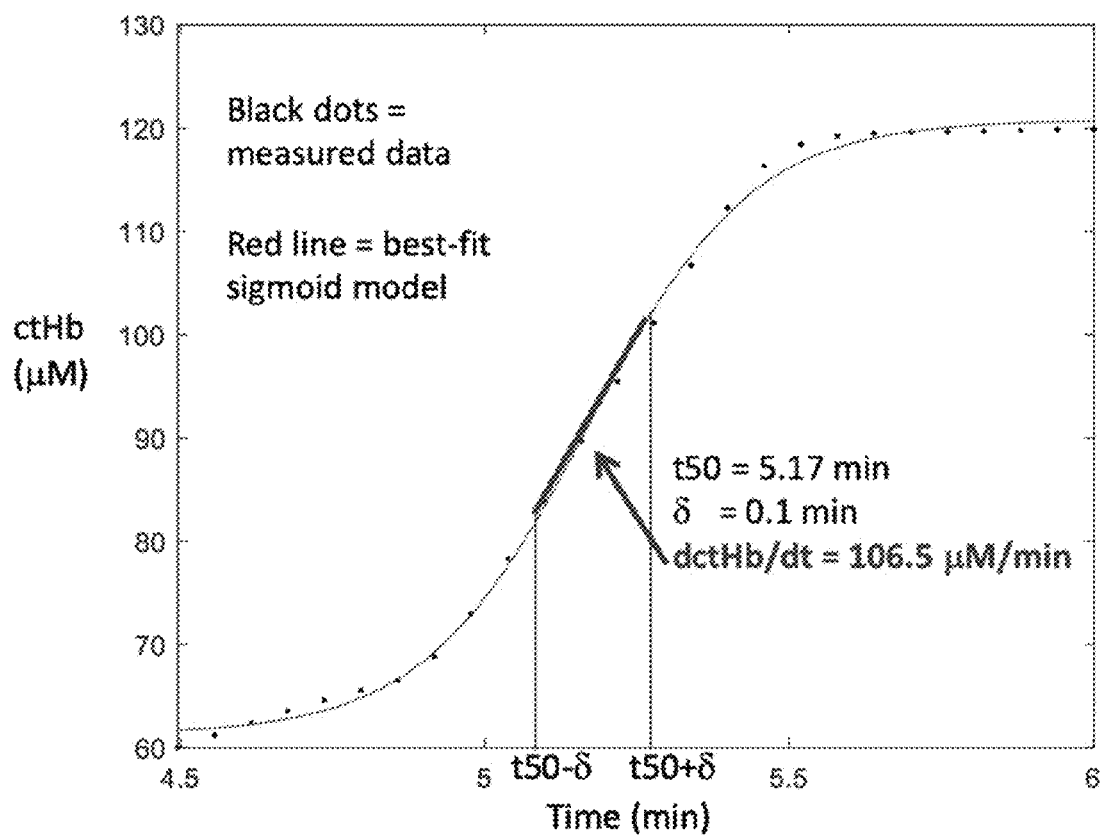

FIG. 13 shows an embodiment where the rate of change of deoxy-hemoglobin concentration in the tissue during the "zero-flow" period is modeled by fitting a sigmoid function to the measured data and then linearizing this sigmoid over a defined time window (which can have the duration shown in the figure or a shorter or longer duration). In another embodiment, the rate of change of deoxy-hemoglobin during the zero-flow period is calculated by choosing the endpoints of the linear period manually and calculating the mean rate of change over that period by calculating the slope of the line segment connecting those two endpoints.

FIG. 14 shows another embodiment where the absolute CMRO2 is calculated without the need for a "zero-flow" condition, thereby significantly reducing the perturbative effect on the tissue. In this embodiment, a dimensional analysis technique is used to combine the blood flow term (in absolute physiological units; e.g., $D_b$ or $v_c$ as described above) with the deoxy-hemoglobin concentration in the tissue and a parameter (delta) describing the mean penetration depth of the light in the tissue. This embodiment was compared with one of the embodiments using the zero-flow condition, showing good agreement between the absolute CMRO$_2$ values for rats during a baseline period under anesthesia (FIG. 8).

Figure 15:
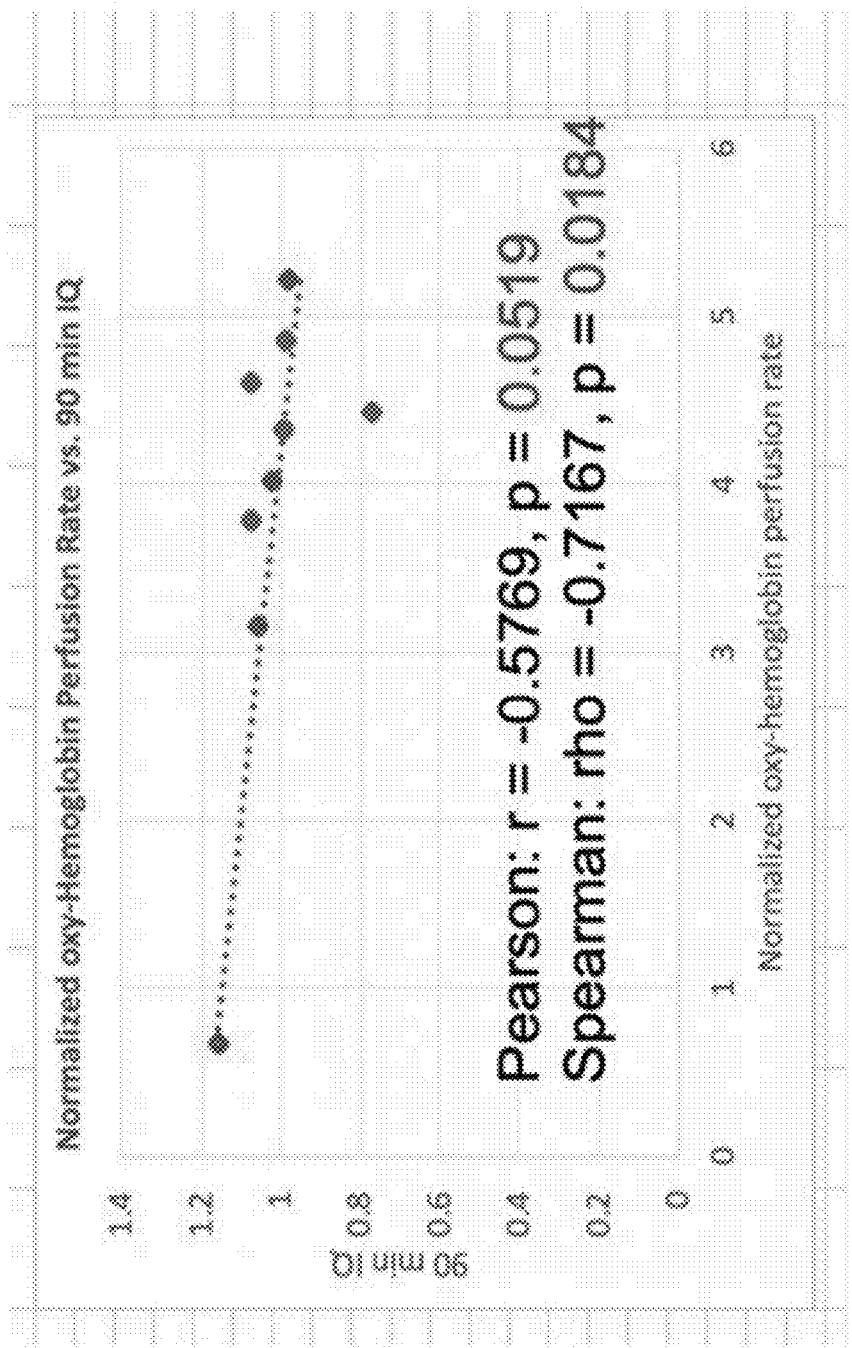

FIG. 15 shows an embodiment of the invention where an oxyhemoglobin perfusion rate *during the first 30 seconds of CPR* is calculated by measuring the oxyhemoglobin concentration with SFDI and determining the mean area under the curve during that time range. This figure shows, surprisingly, that a higher perfusion rate of oxygenated hemoglobin over the *first 30 seconds* of CPR exhibited a significant negative correlation with cerebral electrical recovery (ECoG information quantity) 90 min post-CPR. This result provides evidence that our technology can help to predict the brain's response to CPR, an area that is typically overlooked in current clinical practice.

Figure 16:
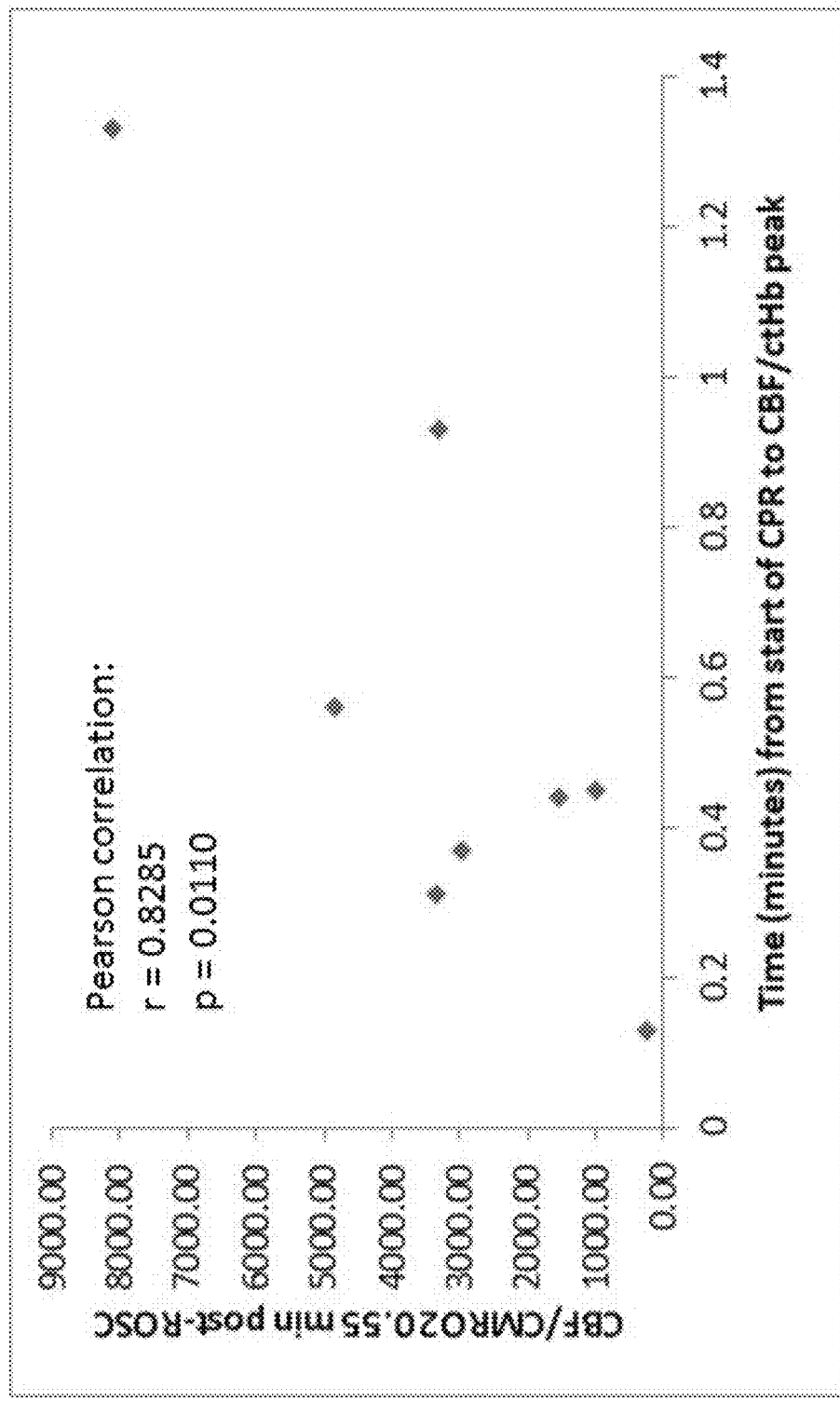

FIG. 16 shows an embodiment where a ratio of two parameters measured continuously *during CPR* (in this case, CBF and brain tissue deoxy-hemoglobin concentration ctHb) is monitored to identify the time it takes for the ratio to reach its peak value. The time (relative to the start of CPR) for this ratio to reach its peak value was strongly correlated with the CBF/CMRO$_2$ ratio 0.55 min *after* CPR. This CBF/CMRO2 ratio in the initial minutes post-CPR was shown to be prognostic of cerebral electrical recovery, as seen in other embodiments described in this patent, and this figure shows that a ratio of this type can be predicted via ratiometric CBF/ctHb data obtained during CPR.

FIGS. 17A-B show a cerebral blood flow (CBF) and mean arterial pressure (MAP) comparison. FIG. 17A shows a representative 5-min asphyxia experiment that shows relative SFI (top) and MAP (bottom) time-course plots. Black vertical line represents start of asphyxia, green vertical line represents return of spontaneous circulation (ROSC) following CPR, and purple vertical line represents stabilized hypoperfusion. The relative SFI time-course shows that CBF is much lower than baseline at stabilized hypoperfusion, while the MAP is close to baseline at stabilized hypoperfusion. The gap from ~21- to 23-min on the MAP time-course is due to arterial blood gas (ABG) measurement being performed. FIG. 17B shows the same 5-min asphyxia experiment from FIG. 17A that compares MAP and relative SFI before stabilized hypoperfusion (blue) and after stabilized hypoperfusion (red). Before stabilized hypoperfusion, MAP and relative SFI are significantly correlated for the representative rat (R=0.77, p=1×10$^{-93}$). After stabilized hypoperfusion, CBF is at a major deficit compared to baseline, while MAP is maintained near baseline (set of points circled in red).

FIGS. 18A-G show that resumption of EEG activity ("bursting") begins during the transition between the CBF hyperemic phase and the stabilized hypoperfusion phase. FIG. 18A shows representative relative SFI and EEG time-courses to illustrate initial EEG burst occurs after CBF hyperemic phase and before stabilized hypoperfusion. EEG data shown was recorded from the upper-left electrode in FIG. 1(C). Black vertical line represents start of asphyxia, green vertical line represents ROSC, and red vertical line represents initial EEG burst. (FIGS. 18B and 18C) area under curve (AUC) from ROSC to burst vs time to burst after ROSC shows a significant positive correlation for relative SFI (left) (R=0.84, p=0.0003) and MAP (right) (R=0.80, p=0.001). (FIGS. 18D and 18E) AUC from ROSC to burst is significantly less for 5-min asphyxia than 7-min asphyxia for relative SFI (left) (1290±140 vs 1781±286, p=0.002) and non-significantly time-integrated MAP (right) (1331±257 vs 1645±378, p=0.1). (FIGS. 18F and 18G) The predictive burst ratio was similar for 5- and 7-min asphyxial durations for relative SFI (left) (258.0±28.1 vs 254.5±40.8, p=0.86) and MAP (right) (269.7±47.5 vs 249.7±43.3, p=0.45). Asterisks represent significant differences (p<0.05).

FIGS. 19A-D show representative measured ("actual") and predicted times of initial EEG burst using a linear regression model where the independent variable is the predictive burst ratio from 0.25-6 min post-ROSC and the dependent variable is the time from ROSC to initial EEG burst. FIG. 19A shows a representative 5-min asphyxial experiment that used relative SFI data to predict the initial EEG burst time, with a percent error of 3.42% obtained. FIG. 19B shows the same 5-min asphyxial experiment as FIG. 19A, but with MAP used for predicting initial EEG burst time, with a percent error of 12.10% obtained. FIG. 19C shows a representative 7-min asphyxial experiment that used relative SFI to predict initial EEG burst time, with a percent error of 39.37% obtained. FIG. 19D shows the same 7-min asphyxial experiment as FIG. 19C, but with MAP used for predicting initial EEG burst time, with a percent error of 52.96% obtained.

DETAILED DESCRIPTION OF THE INVENTION

Since the discovery of CPR, resuscitation guidelines have not changed much, consisting mostly of various combinations 1) chest compressions at a suggested rate and depth to optimize systemic perfusion, 2) ventilation at a frequency and volume to provide for systemic oxygenation and removal of carbon dioxide, and 3) pharmacologic agents such as epinephrine or other cardiovascular medication to promote resuscitation. The focus of perfusion and oxygenation is typically on the coronary arteries of the heart, which is often the source of the cardiac arrest. However, in recent decades, it has become evident that after proper cardiac resuscitation and return of spontaneous circulation (ROSC), the biggest determinant of outcome becomes the neurological system and how much potential anoxic brain injury occurred during the cardiac arrest as well as the level of reperfusion injury in the brain during CPR and post-ROSC time periods.

The American Heart Association has done comprehensive review of the literature on studies focusing on post-cardiac arrest blood pressure targets. While the evidence supports targeting a minimum mean arterial pressure (MAP) of >65 mmHg and/or a systolic blood pressure (SBP) of >90 mmHg, and some isolated studies do support targeting a slightly higher MAP, there is no overwhelming evidence nor wide agreement on targeting a specific blood pressure. Many of these studies cite poor end-organ data, such as cerebral perfusion and cerebral oxygenation, to enable targeting a specific systemic blood pressure. As such, many ongoing trials and the overall direction of this important area of research have began appreciating that more data is needed on providing adequate but not excess perfusion and oxygenation to the brain. Equally important is the fact that essentially none of these prior studies capture data in the moments during CPR and in the immediate minutes post-ROSC. Rather, they capture and report data typically well beyond the first 30 minutes or 1 hour post-ROSC, when the patients are often admitted to the intensive care unit and monitored closely. The present invention targets precisely this huge unmet clinical need: the critical importance of capturing brain perfusion and oxygenation during CPR and in the immediate minutes post-ROSC, which offer multiple transient opportunities for intervention.

The present invention provides data to support the novel discovery that specific parameters, namely the cerebral blood flow, cerebral oxygenation, and cerebral metabolism are of critical importance 1) during the moments of CPR onset, 2) during ongoing CPR, 3) during the immediate minutes post-ROSC, and 4) within the first 30-60 minutes post-ROSC. Interestingly, we will designate time period (5) as any time after ~1 or 2 hours post-ROSC, which is the typical time period reported in the vast majority of literature described above, including in consensus guidelines such as by the widely respected AHA. In this invention, we demonstrate data on the period typically overlooked (i.e. periods 1-4) with our data supporting a specific CBF/CMRO2 target during (1), (2), and (3), and a specific CBF target during (4). Because the data we present is mostly from small animal models, the time scales in larger animals and humans may vary. For example, in our rodent data, time period (1) pertains to the initial 15-30 seconds after initiation of CPR, (2) pertains to any period during CPR after 15-60 seconds until the cessation of CPR until ROSC is achieved, (3) pertains to 30 seconds to 3 minutes after ROSC, and (4) pertains to the period of time approximately 5-20 minutes after ROSC. However, in humans, due to differences in bodily metabolism, it is very likely that these time periods are different, such that (1) may be longer than 15-30 seconds (e.g. 30 seconds-5 minutes), (2) may be in the range of >1-5 minutes during CPR, (3) may be 1-5 minutes after ROSC, and (4) may be 5-45 minutes after ROSC. The precise values in the human species are still being determined because of the lack of data in humans during these time periods, which underscores the importance of our invention that these time segments are typically overlooked in current and past studies focusing on this important area of research.

While the systemic perfusion (e.g. MAP or SBP) and the system oxygenation are important, this may or may not be adequate to optimize cerebral perfusion and oxygenation, supporting the importance of advanced monitoring techniques for the brain during resuscitation. The target values for these brain parameters may be different at each of these segments in time, and they should be targeted on an individual subject basis based on data obtained from each subject during the ongoing resuscitation. For this reason, we propose real-time, precision-guided CPR that utilizes techniques for optimization of the brain's blood flow and metabolism that can optimize neurological recovery after cardiac arrest. While the ultimate potential and goal of the present invention is to guide ongoing treatment to optimize neurological recovery, this method also allows for real time diagnosis (e.g. during ongoing resuscitation and post-resuscitation moments) and prognosis of the level of anoxic brain injury (e.g. a marker of brain injury).

In short, the present invention offers unique opportunities during previously overlooked time segments during and immediately after cardiac arrest and resuscitation for the diagnosis, prognosis, and treatment of cardiac arrest and resuscitation. These transient opportunities for monitoring and possible intervention are in the immediate seconds and minutes during CPR and the immediate minutes post-ROSC and provide a novel basis for our invention to enable better diagnosis, prognosis, and most importantly, better outcome after cardiac arrest.

In one potential embodiment, a patient who has undergone cardiac arrest and been resuscitated successfully with CPR may undergo continuous monitoring of cerebral blood flow throughout the period post-ROSC. The cumulative area under the curve of the CBF for this patient can be continuously calculated (e.g., over the first few minutes post-ROSC) and inputted into a predictive model (based on a linear regression, non-linear regression, or multivariate regression combined with other variables such as MAP, tissue oxygenation, and CMRO2) to prognosticate (with real-time feedback) the expected time at which EEG bursting will resume. If the model predicts that resumption of bursting will be significantly delayed, interventions can be performed to modulate the peripheral blood pressure and/or cerebral blood flow to hasten the predicted burst time, thereby facilitating improved recovery of the brain. Aside from guidance of treatment, prognostication may be improved when the patient's family and surrogate decision-makers are requesting an update on the patient's status, especially if they are considering goals of care (i.e. whether the patient has a good or poor prognosis). Specifically, our invention may allow predicting whether or not and when the EEG may begin bursting with a certain probability, and this information can be conveyed in layman's term to the family and surrogates.

In another potential embodiment, a patient who has undergone cardiac arrest and been resuscitated successfully with CPR may undergo continuous monitoring of cerebral blood flow and cerebral metabolic rate of oxygen throughout the period post-ROSC. Using these measurements, the ratio between cerebral blood flow and metabolism can be continuously calculated and used to provide real-time feedback about the recovery of the brain. If the flow/metabolism ratio is too low (e.g., <1), interventions to increase cerebral perfusion can be performed so that blood flow in the brain can meet metabolic demand. If the flow/metabolism ratio is too high (e.g., >>1), interventions to decrease cerebral perfusion can be performed to avoid excessive perfusion and buildup of un-metabolized oxygen. These interventions can be modified again and again over time in a real-time feedback method if necessary to continuously adjust the flow/metabolism ratio as the patient is recovering to ensure that the flow and metabolism are matched. It is also possible to develop a closed-loop system to automate the treatment adjustments (e.g. increasing or decreasing medication) based on the flow/metabolism ratio to maximize usage of the information, which may be very dynamic.

In another potential embodiment, a patient who is at high risk of undergoing cardiac arrest can receive continuous monitoring of cerebral blood flow and brain oxygenation. If this patient enters cardiac arrest, these continuous readings of perfusion and oxygenation can be used to provide real-time feedback to inform a "brain-targeted CPR" approach where variables such as the duration of compressions, depth of compressions, and level of oxygen as well as depth/volume of ventilation administered to the patient can be modulated during the CPR period itself to optimize perfusion while simultaneously avoiding hyper-oxygenation of the brain or hyperventilation, to improve probability of successful resuscitation and better recovery of the brain post-ROSC. Of note here is that not only can hyper-oxygenation (too much oxygen) be harmful, but hyperventilation (leading to low carbon dioxide) can potentially be harmful also. Hyperventilation can cause vasoconstriction and less blood flow in the brain and other organs. During brain ischemia, hyperventilation may worsen blood flow further. Thus, during CPR, the present invention has implications for total perfusion in the brain and how the ventilation can be adjusted to maximize the needs of the patient in real-time. In this way, optimizing both oxygenation and ventilation (carbon dioxide) enables health care providers to maximize chances for survival and optimal recovery.

In another embodiment, in the hospital, a patient that lacks any brain monitoring may suffer a cardiac arrest wherein a "code blue" is called while a health care provider (e.g. bedside nurse) may initiate CPR. The code blue team may arrive and take over the CPR. Before the code blue team takes over the CPR, they could attach brain sensors to capture the brain perfusion and brain metabolism either during the ongoing CPR or in between CPR providers switching or during the cardiac rhythm assessment (e.g. 5-10 second pause) before a shock may or may not be delivered. The brain sensors would capture brain perfusion and brain metabolism metrics in either relative or absolute measures which can then inform the code blue team on how to conduct the CPR. For example, if they found brain oxygenation or the oxy-hemoglobin perfusion rate is too high, they can inform the team to reduce the oxygen content in the bag-valve-mask. While ensuring that the coronary arteries are getting sufficient perfusion and the peripheral blood pressure is satisfactory during the compressions, if the brain perfusion may be too high, the code blue team can reduce the depth of the chest compressions as long as the coronary perfusion remains satisfactory. Also, the code blue team may decide to alter the brain metabolism without modulating the brain perfusion. For example, the brain metabolism may be reduced more by sedatives, anesthetics, or other pharmacologic agents to adjust the CBF/CMRO2 ratio in more ways than one. Once the patient achieves ROSC, the next few minutes would remain critical, and the code blue team would stay to ensure that the brain perfusion and metabolism remains optimal in these critical minutes. Typically, the code blue team may leave after the patient achieves ROSC. In this example, the code blue team should only leave after consulting another team, such as a neurology or critical care team to continue managing the brain perfusion and metabolism for the next few hours to continue optimizing neurological outcome.

In the said embodiment, the patient may not be in the hospital but outside. In such an out-of-hospital cardiac arrest, a bystander may initiate CPR while asking another bystander to bring the nearest Automated External Defibrillator (AED). Next to the AED could be another device that includes brain sensors that are applied to the patient simultaneously when the AED is placed. Just as the AED assesses the cardiac rhythm and informs the bystander to perform a shock or not to defibrillate the heart, the brain sensor device would assess the brain perfusion and metabolism and inform the bystander on the quality of their compressions—depth, rate, and synchronicity. If ventilation is also being performed by the same bystander or another bystander, the brain sensor device may also inform that person to adjust the ventilation—volume of air, rate, and overall optimal gas exchange. If supplemental oxygen is being delivered rather than room air, the brain sensor device can also inform the amount of supplemental oxygen that should be delivered during the ventilation. When paramedics arrive, they can be updated on the brain sensor device to continue optimizing CPR. The patient would be transported to the hospital with said brain sensor device where CPR continues to be optimized to protect the brain from ischemia, hyperperfusion, or hyperoxygenation. Upon arrival to the hospital, the information is conveyed from the paramedics to the hospital staff, and the hospital staff would continue optimizing CPR if still needed. After the patient achieves ROSC, the brain sensor device would continue to gather information and inform the staff on management of the brain perfusion and metabolism for the immediate minutes and upcoming hours so that the patient can have the best chance of optimal neurological recovery. This information can also be used at any time to guide prognostication and provided to family member or surrogates to help in their decision-making for goals of care. For example, if all the metrics obtained from the brain sensor forebode a very poor outcome, this information can be examined in the context of other medical information (e.g. neurological exam, EEG, CT scan, blood work, etc.) and all provided to the family or surrogate to allow them to make the best decision about the goals of care. In no way is this embodiment limited to cardiac arrest as it may apply to other types of acute brain injury (e.g. ischemic or haemorrhagic stroke, subarachnoid haemorrhage, traumatic brain injury, other) where there are other ways to modulate the brain perfusion and metabolism beyond CPR and artificial ventilation. For example, if the patient is not in a cardiac arrest, their brain perfusion can still be modified through numerous other ways, including but not limited to pharmacologic agents, intravenous fluids, body positioning, or breathing techniques. In this way, this invention can assist a variety of different acute brain injuries beyond cardiac arrest and improve the diagnosis, treatment, and prognosis of a patient that may benefit from measurement of the brain perfusion and metabolism.

In one embodiment, the present invention features a method of performing guided, brain-targeted cardiopulmonary resuscitation (CPR) on a subject. As a non-limiting example, the method of the present invention may be able to direct CPR variables in real time based on brain oxygen supply and utilization. Guided brain-targeted CPR may be advantageous because many CA patients suffer significant long-term neurological damage, likely in part because very little is known about how to optimize perfusion and metabolism of the brain during CPR within the critical first few minutes post-CPR. Typically, CPR is not brain-targeted, as in the present invention, because standard CPR is focused nearly exclusively on the performance of the heart (using feedback given by monitoring of heart rate and peripheral blood pressure). Therefore, this embodiment "teaches away" from commonly-accepted CPR practices by providing a complementary CPR paradigm where continuous feedback on brain hemodynamics is incorporated into the CPR workflow to optimize CPR quality to target the brain in addition to the heart.

In some embodiments, the present invention allows for evaluation of a brain which has experienced an ischemic event, prior to the return of spontaneous circulation (ROSC) As a non-limiting example, the present invention may feature a method of evaluating the cerebral blood flow, brain oxygen supply, and brain oxygen utilization after an ischemic event, prior to ROSC. This may be advantageous to diagnose severity and duration of injury (e.g., amount of "down-time" that has passed between when the event occurred and when the event was identified). Other techniques cannot provide such evaluation because they do not provide continuous monitoring of multivariate flow-metabolism metrics to simultaneously diagnose injury and prognosticate recovery during this critical ultra-early time window.

In some embodiments, the present invention may require the determination of a brain perfusion value and a brain metabolism value. Non-limiting examples of brain perfusion values include, cerebral blood flow (CBF), speckle flow index (SFI), blood flow index (BFI), Brownian diffusion coefficient Db, and directed-flow coefficient vc. Non-limiting examples of brain metabolism values include, cerebral metabolic rate of oxygen ($CMRO_2$), deoxy-hemoglobin concentration ctHb, and brain oxygenation StO2. The brain perfusion value and the brain metabolism value may each be a relative value in comparison to a baseline value, or alternatively, the brain perfusion value and the brain metabolism value may each be an absolute value. This allows for longitudinal comparison between subjects and a given subject at multiple discrete time points separated by hours, days, months, or even years, using the metric of absolute CMRO2.

Figure 1A:
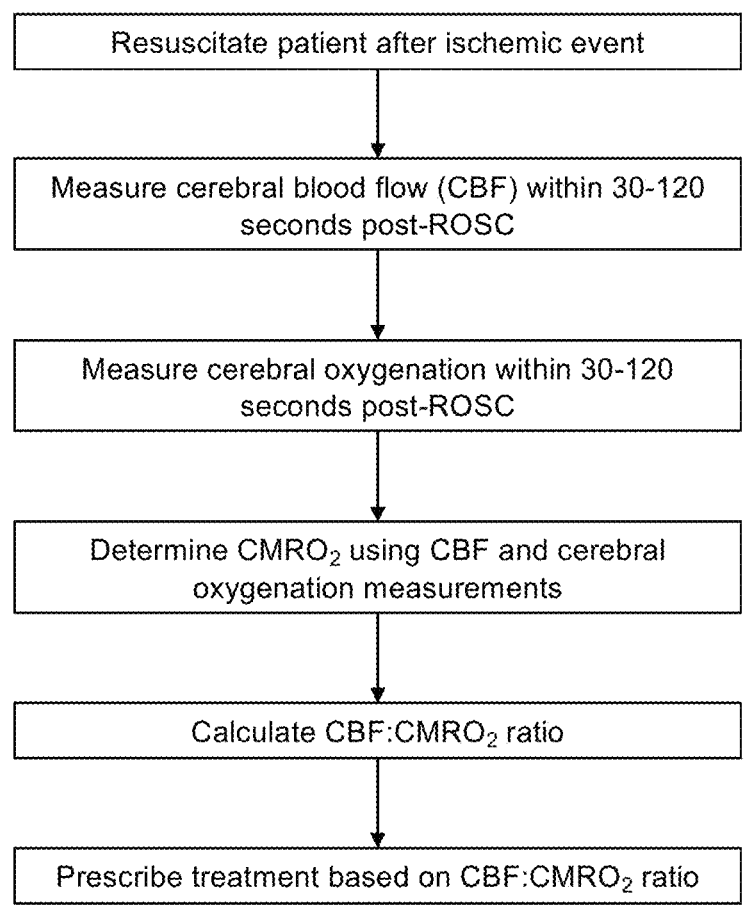

Referring now to FIG. 1A, the present invention may feature a method of determining brain damage severity and prognosing recovery after an ischemic event in a subject. In one embodiment, the method may comprise measuring cerebral blood flow (CBF), measuring cerebral oxygenation, determining a relative cerebral metabolic rate of oxygen ($CMRO_2$) using the measurements of CBF and cerebral oxygenation, and calculating a ratio of the CBF to $CMRO_2$.

According to another embodiment, the present invention provides a method of treating brain damage in a subject that experienced an ischemic event. The method may comprise resuscitating the subject after the ischemic event, measuring cerebral blood flow (CBF) and cerebral oxygenation within a specific period of time immediately post-resuscitation, determining a relative cerebral metabolic rate of oxygen ($CMRO_2$) using the measurements of CBF and cerebral oxygenation, calculating a ratio of CBF to $CMRO_2$, and prescribing a treatment based on the CBF:$CMRO_2$ ratio. In some embodiments, the prescribed treatment may be a pharmaceutical composition, surgery, rehabilitative therapy, or a combination thereof.

In one embodiment, the $CMRO_2$ may be calculated using the equation: $1+rCMRO_2=(1+\Delta CBF/CBF_o)(1+\gamma_r\Delta ctHb/ctHb_o)(1+\gamma_t\Delta ctHb_{tot}/ctHb_{tot,o})^{-1}$, where $\Delta CBF$, $\Delta ctHb$, and $\Delta ctHb_{tot}$ are changes in CBF, deoxy-hemoglobin, and total hemoglobin, respectively, relative to their baseline values, $CBF_0$, $ctHb_0$, $ctHbtot_0$, wherein $\gamma_r$ and $\gamma_t$ are set to 1.

Without wishing to limit the invention to a particular theory or mechanism, the CBF:$CMRO_2$ ratio taken within a specific period of time after resuscitating the subject can provide a severity assessment and recovery prognosis for the subject, thus the method can improve cerebral recovery of the patient. The specific period of time is preferably less than 3 minutes, for example, 30-120 seconds. In some embodiments, if the CBF:$CMRO_2$ ratio is at or below a first threshold, the ratio is indicative of ischemic damage. In one embodiment, this first threshold may be about 1-1.2. If the CBF:$CMRO_2$ ratio is above a second threshold that is higher than the first, the ratio is indicative of excess perfusion. The second threshold may greater than or equal to 1, for example the second threshold is 1.2.

In other embodiments, the method may further comprise measuring cerebral electrical activity as electrocorticography (ECoG) bursts immediately post-resuscitation. Without wishing to be bound to a particular theory or mechanism, the CBF:$CMRO_2$ ratio is predictive of ECoG burst time. In one embodiment, a higher CBF:$CMRO_2$ ratio immediately after resuscitation is associated with a shorter asphyxial cardiac arrest period and improved neurological outcome as measured by faster ECoG bursting.

In some embodiments, the step of measuring CBF, cerebral metabolism, and ECoG bursts may comprise illuminating a target tissue of the subject using a laser light source of a laser speckle imaging (LSI) system, detecting remitted light from the target tissue using a first detector of the LSI system and recording measurements of the remitted light, projecting spatial frequency patterns of light onto the target tissue using a spatial light modulator coupled to a plurality of light emitting diodes (LEDs) of a spatial frequency domain imaging (SFDI) system, detecting backscattered light from the target tissue using a second detector of the SFDI system and recording measurements of the backscattered light, detecting cerebral electrical activity of the subject using electrodes of an ECoG system and recording ECoG burst frequency, calculating speckle flow index (SFI) values using the LSI measurements to obtain CBF measurements, and determining deoxyhemoglobin and hemoglobin concentrations from the SFDI measurements. The relative $CMRO_2$ is calculated using the CBF measurements and deoxyhemoglobin and hemoglobin concentrations. In other embodiments, other technology besides LSI and SFDI may be used to achieve the same end-information used to estimate or accurately measure the CBF, oxy-hemoglobin, deoxy-hemoglobin, total hemoglobin, brain oxygen saturation, edema, and either relative or absolute CMRO2. In no way does our invention limit the techniques to LSI and SFDI providing this information.

In preferred embodiments, the method is non-invasive and can provide information about the brain in the immediate minutes post-reperfusion. In some embodiments, the ischemic event is cerebral ischemia caused by cardiac arrest, stroke or traumatic brain injury. As another example, the ischemic event includes global ischemia from cardiac arrest.

According to some embodiments, the present invention features a system for determining brain damage severity and prognosing recovery after an ischemic event in a subject. The system may comprise a means for measuring cerebral blood flow (CBF), a means for measuring cerebral metabolism, and a processing unit comprising a memory and a processor operatively coupled to the memory. The memory stores computer-readable instructions that when executed by the processor, causes the processor to perform operations comprising determining a relative cerebral metabolic rate of oxygen ($CMRO_2$) using the measurements of CBF and cerebral oxygenation, and calculating a ratio of the CBF to $CMRO_2$. In other embodiments, the system may further comprise a means for measuring ECoG burst frequency for cerebral electrical activity, where the $CBF:CMRO_2$ ratio is predictive of ECoG burst time.

Figure 1B:
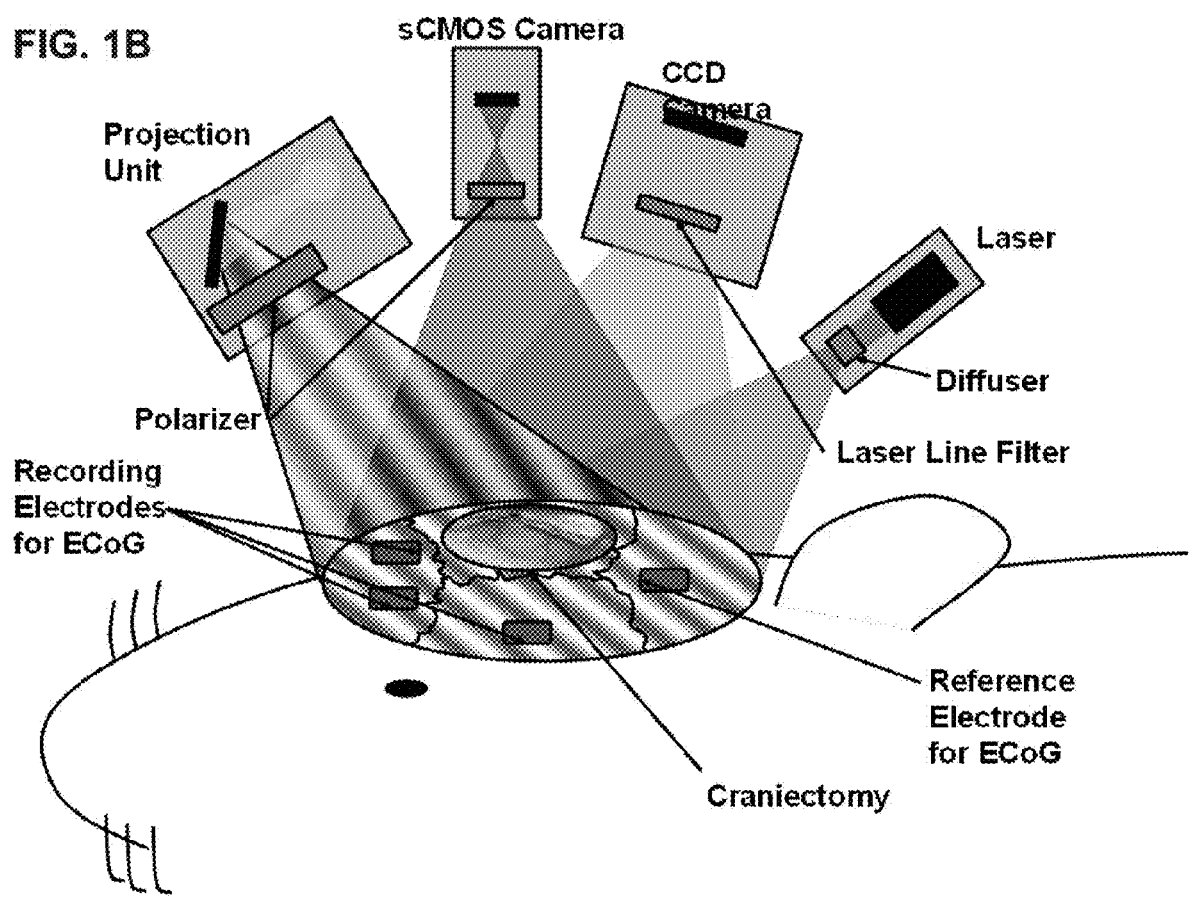

An example of the system for determining brain damage severity and prognosing recovery after an ischemic event in a subject is shown in FIG. 1B. In some embodiments, the system may comprise a laser speckle imaging (LSI) system comprising a laser light source, a diffuser, and a first detector; a multispectral spatial frequency domain imaging (SFDI) system comprising a plurality of light emitting diodes (LEDs) of varying wavelengths, a spatial light modulator coupled to the LEDs, and a second detector; an electrocorticography (ECoG) system comprising a plurality of electrodes; and a processing unit comprising a memory and a processor operatively coupled to the memory, the LSI system, the SFDI system, and the ECoG system. In some embodiments, the laser light source may be an 809 nm laser.

In other embodiments, the plurality of LEDs may comprise 655 nm, 730 nm, and 850 nm LEDs or LEDs using other appropriate wavelengths.

In one embodiment, the memory can store computer-readable instructions that when executed by the processor, causes the processor to perform operations comprising recording ECoG burst frequency from the ECoG system, which correlates to cerebral electrical activity, recording measurements from the LSI system, calculating speckle flow index (SFI) values using the LSI measurements to obtain measurements of cerebral blood flow (CBF), recording measurements from the SFDI system, determining deoxyhemoglobin and hemoglobin concentrations from the SFDI measurements, calculating a relative cerebral metabolic rate of oxygen ($CMRO_2$) using the CBF measurements and deoxyhemoglobin and hemoglobin concentrations, and calculating a ratio of the $CBF:CMRO_2$. Without wishing to limit the present invention, the $CBF:CMRO_2$ ratio can quantify a degree of mismatch between cerebral perfusion and metabolism, and also serve as a metric of cerebral autoregulation. For instance, within a specific period of time after resuscitation, the $CBF:CMRO_2$ ratio can be used to provide a severity assessment and recovery prognosis, as well as predict ECoG burst time.

In other embodiments, the present invention may incorporate fiber-probe based methods to interrogate regions of the brain that are deeper beneath the surface. In yet other embodiments, non-invasive near-infrared spectroscopy (NIRS) and coherent optical fluctuation sensing techniques, such as for example diffuse correlation spectroscopy (DCS) and Doppler-based techniques, may be applied to measure CBF and $CMRO_2$ immediately post-ROSC in CA patients.

As will be further detailed in the following example, the system of the present invention may be used in a method of determining brain damage severity and prognosing recovery after an ischemic event in a subject. The method may comprise illuminating a target tissue of the subject using the laser light source of the LSI system, detecting remitted light from the target tissue using the first detector of the LSI system and recording measurements of the remitted light, projecting spatial frequency patterns of light onto the target tissue using the spatial light modulator coupled to the plurality of light emitting diodes (LEDs) of the SFDI system, detecting backscattered light from the target tissue using the second detector of the SFDI system and recording measurements of the backscattered light, detecting cerebral electrical activity of the subject using the ECoG system and recording ECoG burst frequency, calculating SFI values using the LSI measurements to obtain CBF measurements, determining deoxyhemoglobin and hemoglobin concentrations from the SFDI measurements, calculating the relative $CMRO_2$ using CBF measurements and deoxyhemoglobin and hemoglobin concentrations, and calculating the $CBF:CMRO_2$ ratio.

As another non-limiting example, a method of determining brain damage severity and prognosing recovery (e.g. after an ischemic or ischemic and reperfusion event in a subject) may include illuminating a target tissue of the subject using one or more light sources of a diffuse optical measurement system to enable direct or surrogate measures of flow or pressure. In some embodiments, one or more of the light sources may be laser light sources. As non-limiting examples, the diffuse optical measurement system may include a laser speckle imaging (LSI) system, a diffuse correlation spectroscopy (DCS) system, another flow measurement technology such laser Doppler flowmetry (LDF), or tissue reflectance measured with a coherent or incoherent source measured at multiple wavelengths, multiple temporal or spatial frequencies, or multiple spatial positions or time gates. These embodiments may be invasive or non-invasive.

The method of determining brain damage severity and prognosing recovery may also include detecting remitted light from the target tissue using a first detector of the system and recording measurements of the remitted light. Furthermore, the method of determining brain damage severity and prognosing recovery may also include projecting spatial frequency patterns of light onto the target tissue using a spatial light modulator coupled to a plurality of light emitting diodes (LEDs) of a spatial frequency domain imaging (SFDI) system, or optically interrogating the tissue using diffuse optical spectroscopy (DOS), near-infrared spectroscopy (NIRS), frequency-domain photon migration DOS (FDPM-DOS), frequency-domain photon migration NIRS (FDPM-NIRS), time-resolved diffuse optical spectroscopy (TR-DOS) or time-resolved near-infrared spectroscopy (TR-NIRS) system, or any combination of these technologies, using one or more wavelengths in the visible, near-infrared, or short-wave infrared region (~400-1800 nm).

The method of determining brain damage severity and prognosing recovery may also include detecting backscattered light from the target tissue using the system and recording measurements of the backscattered light. In some embodiments, the method of determining brain damage severity and prognosing recovery may also include detecting cerebral electrical activity of the subject using an electrocorticography (ECoG) or electroencephalogram (EEG) system and recording a variety of quantitative ECoG or EEG algorithms or metrics including but not limited to ECoG or EEG power, burst frequency, information quantity, coherence, phase-amplitude coupling, alpha/delta ratio, or other algorithms or metrics that can measure brain electrical activity after reperfusion. Furthermore, these ECoG or EEG metrics can be combined with optical measurements of cerebral blood flow, oxygenation, and metabolism to quantify neurovascular coupling. For instance, the ratio of cerebral blood flow to EEG information quantity can provide another quantitative metric of "supply and demand"; in this case, specifically quantifying the relationship between cerebral perfusion ("supply") and cerebral electrical activity ("demand"). Also, real-time feedback can be obtained from the quantitative ECoG or EEG algorithm or metric that can then inform the health care provider to focus on one of the optical measures and modify therapy. For example, if the ECoG or EEG raise concern for spreading depolarizations or repolarizations, the optical scattering can be focused on to reassure, validate, or confirm the diagnosis before treatment is implemented.

The method of determining brain damage severity and prognosing recovery may also include calculating speckle flow index (SFI) values, blood flow index (BFI), Brownian diffusion coefficient (Db), or directed flow speed (vc), or another direct or surrogate measure of flow or pressure using the diffuse optical measurements, wherein the SFI, BFI, Db, or vc values are measurements of cerebral blood flow (CBF). The method of determining brain damage severity and prognosing recovery may also include determining deoxyhemoglobin and hemoglobin concentrations from any of the measurements using modulated light. The method of determining brain damage severity and prognosing recovery may also include calculating a relative cerebral metabolic rate of oxygen ($CMRO_2$) using CBF measurements and deoxyhemoglobin and hemoglobin concentrations; and calculating a ratio of the CBF to $CMRO_2$. In some embodiments, within a specific period of time after resuscitating the subject, the $CBF:CMRO_2$ ratio can provide a severity assessment and recovery prognosis for the subject. As non-limited examples, the specific period of time may be less than 1, 2, 3, 4, 5, 6, 7, 8, 9, 10, 11, 12, 13, 14, 15, 16, 17, 18, 19, 20, 25, 30, 35, 40, 45, 50, 55, or 60 minutes or seconds. As another non-limiting example, the specific period of time may be about 5-60, 10-60, 15-60, 20-60, 25-60, 30-60, 40-60, 50-60, 5-120, 10-120, 15-120, 20-120, 25-120, 30-120, 40-120, 50-120, 60-120, 30-180, 30-240, 30-300, 30-360, 30-420, 30-480, 30-540, or 30-600 seconds or minutes.

Additionally, the $CBF:CMRO_2$ ratio may quantify a degree of mismatch between cerebral perfusion and metabolism, and serve as a metric of cerebral autoregulation. This $CBF:CMRO_2$ ratio may be predictive of ECoG or EEG burst time. In some embodiments if the $CBF:CMRO_2$ ratio is at or below a threshold, the ratio may be indicative of ischemic damage. Furthermore, if the $CBF:CMRO_2$ ratio is above a higher threshold, the ratio may be indicative of excess perfusion. As a non-limiting example, the threshold may be greater than or equal to 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, or 3. In some embodiments, the appropriate threshold value for an individual may be determined based on the data for that individual. In some embodiments, the ischemic event may be cerebral ischemia caused by cardiac arrest, stroke, delayed cerebral ischemia after subarachnoid hemorrhage, or traumatic brain injury.

Without wishing to be bound to a particular theory or mechanism, the present invention has the following advantages over previous technologies:

(1) More quantitative: the present invention uses metrics for both blood flow and oxygenation and combines them into a metabolic and flow-metabolism coupling/uncoupling metric. In further embodiments, the present invention may also incorporate tissue scattering/cytotoxic edema parameters for improved quantitative characterization.

(2) More physiologically relevant: the present invention can quantify autonomic dysregulation in the brain by using flow and metabolism parameters in tandem.

(3) Fast: data are obtained continuously with many data points per second, facilitating rapid diagnosis/prognosis.

(4) Non-invasive: the present invention requires no implantation, no exogenous contrast agents, and can even be non-contact in some manifestations.

In one embodiment, the present invention features a method of performing guided, brain-targeted cardiopulmonary resuscitation (CPR) on a subject. As a non-limiting example, the method may comprise: performing CPR on the subject; simultaneously with CPR (or in a time period shortly after CPR), evaluating cerebral blood flow, brain oxygen supply, or brain oxygen utilization by: determining a brain perfusion value; and determining a brain metabolism value; calculating a ratio R of the brain perfusion value and the brain metabolism value; and directing CPR or post-CPR treatment based on the value of R. The time period shortly after CPR may be within 1, 2, 3, 4, 5, 6, 7, 8, 9, 10, 11, 12, 13, 14, 15, 16, 17, 18, 19, 20, 25, 30, 35, 40, 45, 50, 55, or 60 minutes of return of spontaneous circulation (ROSC).

In some embodiments, CPR may be iteratively directed based on the change of R over time. CPR may be iteratively directed based on a comparison of R or a time-derivative of R to a threshold value. As a non-limiting example, the threshold value may be one. In preferred embodiments, the value of R may be determined dynamically and provide real time feedback. In some embodiments, the value of R may be initially determined within about 20 seconds of beginning CPR. In other embodiments, the value of R may be initially determined within about 2, 4, 6, 8, 10, 12, 14, 16, 18, 22, 24, 26, 28, 30, 40, 50, 60, 70, 80, 90, 100, 110, 120, 150, 175, 200, 250, 300, 350, 400, 450, 500, 550, 600, 650, 700, 750, 800, 850, 900, 950, 1000 or more than 1000 seconds or minutes of beginning CPR.

In one embodiment, the value or change in value of R is used to determine a CPR or post-CPR variable. Non-limiting examples of CPR and post-CPR variables include, a chest compression rate, a chest compression depth, the frequency of ventilation, the depth of ventilation, how much oxygen is administered during each ventilation (including % $FiO_2$ and positive peep end-expiratory pressure), if epinephrine or another pharmacologic agent (e.g. vasodilators, etc.) should be administered, a dose of epinephrine (or other pharmacologic agent) to be administered, if electric shock should be administered, if a pharmaceutical should be administered, or a dose of pharmaceutical to be administered, the position of the patient (e.g. flat, head-up, or other head and bodily position) during CPR, surgical procedures, rehabilitative procedures, another variable, or a combination thereof.

In some embodiments, the brain perfusion value and the brain metabolism value may each be a relative value in comparison to a reference point or baseline value. In alternative embodiments, the brain perfusion value and the brain metabolism value may each be an absolute value. Non-limiting examples of brain perfusion values include cerebral blood flow (CBF), speckle flow index (SFI), blood flow index (BFI), Brownian diffusion coefficient Db, directed-flow coefficient vc, including indirect or surrogate measures of these indices such as tissue hemoglobin concentrations and tissue reflectance, or a combination thereof. In some embodiments, the brain metabolism value may be based on cerebral blood flow, brain oxygenation, a measured concentration of oxyhemoglobin, a measured concentration of deoxyhemoglobin, an indirect or surrogate measure of any of these indices (e.g. tissue hemoglobin concentration or tissue reflectance), or a combination thereof. Non-limiting examples of brain metabolism values include the cerebral metabolic rate of oxygen ($CMRO_2$), the deoxy-hemoglobin concentration ctHb, the tissue oxygenation StO2, an indirect or surrogate measure of any of these indices (e.g. tissue hemoglobin concentration or tissue reflectance), or a combination thereof.

According to one embodiment a device, a probe, a patch, or a sticker which attaches to the subject's body may be used to determine the brain perfusion value, the brain oxygenation value, the brain metabolism value, or a combination thereof. As a non-limiting example, a method for guided CPR may include an initial step of fixing a patch to the subject's head. In one embodiment, a method of the present invention may allow for a CPR pause time (for example, a pause time to check for a pulse) to be reduced or eliminated.

In one embodiment, the present invention features a method of performing guided, brain-targeted cardiopulmonary resuscitation (CPR) on a subject. As a non-limiting example, the method may comprise: performing CPR on the subject; simultaneously with CPR, evaluating brain oxygen supply and utilization by: determining a brain perfusion value; and determining a brain metabolism value; and directing CPR based on both the brain perfusion value and the brain metabolism value. In some embodiments, the brain perfusion value and the brain metabolism value may be analysed as a coordinate (perfusion, metabolism) that uses both the magnitude of each value and the ratio between them to inform CPR.

In another embodiment, the present invention features a method of performing guided, brain-targeted cardiopulmonary resuscitation (CPR) on a subject. As a non-limiting example, the method may comprise: performing CPR on the subject; simultaneously with CPR, evaluating brain oxygen supply and utilization by: determining a brain perfusion value; or determining a brain metabolism value; and directing CPR based on the brain perfusion value or the brain metabolism value.

In yet another embodiment, the present invention features a method of evaluating the brain oxygen supply and utilization of a subject prior to, during, in response to, or after an ischemic event. As a non-limiting example, the method may comprise: determining a brain perfusion value; determining a brain metabolism value; and calculating a ratio R of the brain perfusion value and the brain metabolism value, wherein the value or change in value of R provides information on the relative oxygen supply and utilization of a brain of the subject. In some embodiments, R may be initially calculated prior to, or immediately after, return of spontaneous circulation (ROSC). According to a selected embodiment, R may be calculated during the administration of CPR to the subject.

In some embodiments, the information on the cerebral blood flow, brain oxygen supply, brain oxygen utilization, or a combination thereof may be iteratively used to guide treatment of the subject. In other embodiments, the information on the cerebral blood flow, brain oxygen supply, brain oxygen utilization or a combination thereof may be used to diagnose a condition of the subject or provide prognostication of the patient's cerebral recovery. In still other embodiments, a laser speckle imaging (LSI) system or diffuse correlation spectroscopy (DCS) system or laser Doppler flowmetry (LDF) system may be used to determine the brain perfusion value. According to one non-limiting example, a spatial frequency domain imaging (SFDI), diffuse optical spectroscopy (DOS), near-infrared spectroscopy (NIRS), frequency-domain photon migration DOS (FDPM-DOS), frequency-domain photon migration NIRS (FDPM-NIRS), time-resolved diffuse optical spectroscopy (TR-DOS) or time-resolved near-infrared spectroscopy (TR-NIRS) system, or any combination of these technologies, using one or more wavelengths in the visible, near-infrared, or short-wave infrared region (~400-1800 nm) may be used to determine the brain metabolism value.

EXAMPLE 1

The following is a non-limiting example of the present invention. It is to be understood that said example is not intended to limit the present invention in any way. Equivalents or substitutes are within the scope of the present invention.

Methods

Animal Preparation

All procedures described in this protocol were approved by the Institutional Animal Care and Use Committee (IACUC) at the University of California, Irvine (protocol number 2013-3098-01). Ten male Wistar rats (weight ~300-400 g) were used in this study. In the animal preparation procedures, rats were fasted with three pellets the night before the experiment as standard procedure for the CA experiments. On the day of the experiment, rats were anesthetized with isoflurane and endotracheally intubated to enable controlled breathing with a ventilator. Then, epidural screw electrodes were implanted for ECoG, and a partial craniectomy (4 mm right-to-left×6 mm anterior-to-posterior) was performed to expose a portion of the right sensory and visual cortex for optical imaging. Four epidural screw ECoG electrodes (one of which is the reference electrode) were implanted in the skull. Two of these electrodes were located toward the front of the brain (2 mm anterior to bregma, 2.5 mm lateral to bregma) over the motor cortices, one was located atop the visual cortex (5.5 mm posterior to bregma, 4 mm left of bregma), and the reference electrode was located in the posterior region of the brain (3 mm posterior to lambda), over the cerebellum. The femoral artery was cannulated to enable arterial blood gas sampling as well as blood pressure monitoring while the femoral vein was cannulated to enable intravenous drug delivery.

Laser Speckle Imaging (LSI)

The LSI system employed a long-coherence-length 809 nm laser as the light source. A diffuser was mounted between the laser and the tissue to obtain near-uniform illumination on the exposed brain region. The remitted light was then isolated with a laser line filter and images were acquired at 60 Hz using a CCD camera with an exposure time T of 10 ms. For each region of interest (ROI) selected within the craniectomy, mean speckle flow index (SFI) values were calculated and used to create time-resolved curves. Relative SFI curves were calculated using a sliding median filter of 10 s in length. Unless otherwise specified, the pre-asphyxial time period was chosen as baseline due to post-anesthesia emergence and consequent cerebral hyperemia. However, in a scenario in which pre-CA data is unavailable, a different time period (e.g., post-CPR) can be chosen as the baseline without any loss of validity in the results. The SFI obtained using these procedures was used as the measure of CBF in this report.

Spatial Frequency Domain Imaging (SFDI)

The SFDI setup used three light emitting diodes (LEDs, 655 nm, 730 nm, 850 nm) as light sources that were coupled into a spatial light modulator to project spatial frequency patterns of the light onto the tissue. For detection of back-scattered light, a scientific complementary metal-oxide semiconductor (sCMOS) camera was employed. The acquisition sequence (DC projection, followed by a square-wave pattern at each of three spatial phases, repeated serially over all wavelengths) was repeated to achieve an effective frame rate of ~14 Hz. A two-step fitting procedure was incorporated to arrive at two-dimensional maps of reduced scattering coefficient ($\mu_s'$), oxyhemoglobin concentration (ctHbO$_2$), deoxyhemoglobin concentration (ctHb), total tissue hemoglobin concentration (ctHb$_{tot}$), and tissue oxygen saturation StO$_2$=ctHbO$_2$/ctHb$_{tot}$.

Relative Cerebral Metabolic Rate of Oxygen (rCMRO$_2$) Calculation

The baseline values (ctHb$_0$, ctHb$_{tot,o}$) and changes from baseline ($\Delta$ctHb, $\Delta$ctHb$_{tot}$) in the deoxyhemoglobin and total hemoglobin concentrations from the SFDI measurements were combined with CBF values from the LSI measurements to calculate relative cerebral metabolic rate of oxygen (rCMRO$_2$), using Equation 1:

$$1+rCMRO_2=(1+\Delta CBF/CBF_o)(1+\gamma_r\Delta ctHb/ctHb_o)(1+\gamma_t\Delta ctHb_{tot}/ctHb_{tot,o})^{-1}. \quad (1)$$

In Equation 1, $\Delta$CBF, $\Delta$ctHb, and $\Delta$ctHb$_{tot}$ are the changes in CBF, deoxy-hemoglobin, and total hemoglobin, respectively, relative to their baseline values (CBF$_0$, ctHb$_0$, ctHb-tot$_0$). The constants $\gamma_r$ and $\gamma_t$ are related to the venous and arterial contributions to hemoglobin content, and were set to 1. As was the case for the CBF data, a pre-asphyxial time period was chosen as the baseline for the CMRO$_2$ calculation unless otherwise specified. However, in a scenario in which pre-CA data is unavailable, a different time period (e.g., post-CPR) can be chosen as the baseline without any loss of validity in the results.

Definitions of flow-metabolism mismatch, coupling, and uncoupling

The flow-metabolism ratio CBF/CMRO$_2$ was calculated at each time point by dividing the CBF value obtained with LSI by the CMRO$_2$ value obtained from Equation 1. This ratio was used to quantify flow-metabolism mismatch. Specifically, CBF/CMRO$_2$>1 corresponded to a mismatch for which CBF exceeded metabolic demand, and CBF/CMRO$_2$<1 represented a mismatch where CBF was insufficient to meet metabolic demand. Separately, the periods of flow-metabolism coupling were defined as time windows during which CBF and CMRO$_2$ exhibited similar rates of change, and the periods of flow-metabolism uncoupling were defined as time windows during which the slopes of CBF and CMRO$_2$ had opposite signs, or where one slope was non-zero and the other was zero.

Electrocorticography (ECoG)

Each screw electrode was connected to a Tucker-Davis Technologies (TDT) PZ2 preamplifier, which had a 0.35 Hz high-pass filter for detection of standard ECoG signals. A noise test was performed to ensure that the signal-to-noise ratio was suitable for measurements. Raw ECoG data were processed using custom MATLAB code. DC bias was removed by de-trending the data. Noise and artifacts across channels were reduced with common average referencing. A 60 Hz notch filter and a 1-150 Hz bandpass filter were applied to the data. To lessen computational burden, signals were down sampled to 600 Hz. ECoG burst frequency (defined as bursts/min) was used as a metric to quantify the extent of cerebral electrical recovery, which correlates to neurological outcome.

Cardiac Arrest (CA) and Cardiopulmonary Resuscitation (CPR)

At the beginning of the CA/CPR experiment, the isoflurane level was decreased from 2.0% to 0.5-1.0% and the inhaled gas mixture changed from 50% O$_2$+50% N$_2$ to 100% O$_2$. After two min, isoflurane delivery was turned off and washed out by delivering room air (21% O$_2$). This washout period is essential to mitigate effects of isoflurane on CBF and brain function. During this period, a neuromuscular blocking agent (1 mL of 2 mg/kg Vecuronium; 1 mL of heparinized saline) was administered intravenously to provide the ventilator with complete control of respiration. After three min, asphyxia was induced by turning off the ventilator for a fixed time period of 5 or 7 min, causing progressive hypoxic hypercarbic hypotension. CA was identified when pulse pressure <10 mmHg and systolic pressure <30 mmHg. These conditions mimic pulseless electrical activity, a common type of CA.

Forty-five seconds prior to starting CPR, the ventilator was re-started with 100% oxygen given to the animal (respiratory rate=85 breaths/min, PIP=17.5-18.5 cmH$_2$O, PEEP=3 cmH$_2$O at 2.5 LPM). Immediately before initiating CPR, intravenous administration of 0.01 mg/kg epinephrine, 1 mmol/kg sodium bicarbonate, and 2 mL of heparinized saline was performed. Then, CPR was conducted via external/closed chest compressions until return of spontaneous circulation (ROSC) was achieved (as determined by the blood pressure measured from the femoral artery). The duration of CPR was typically ~1 min. After ROSC, continuous monitoring (blood pressure, heart rate, ECoG, LSI, SFDI) of the animal was performed for ~1.5-2.0 hrs, followed by euthanasia with pentobarbital. FIG. 1B shows the optical imaging and ECoG setup for these experiments.

Results

Spatial Mapping of Cerebral Perfusion and Oxygen Extraction in CA/CPR Model

Figure 1C:
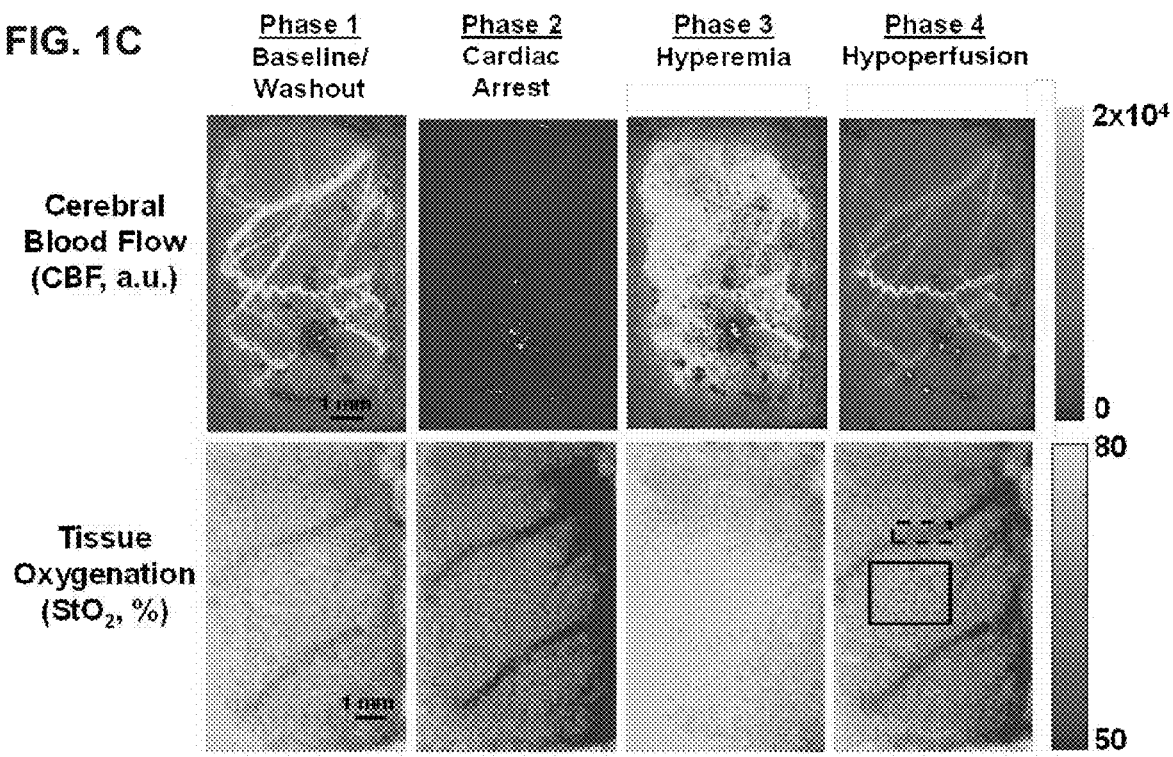

FIG. 1C shows representative maps of CBF and brain oxygenation during four distinct phases of the CA/CPR experiment. During Phase I (baseline/washout), CBF and oxygenation were constant until isoflurane washout began, at which point the CBF and CMRO$_2$ both increased as the animal began to wake up. During Phase II (CA), asphyxia led to a rapid decrease in CBF and oxygenation due to progressive development of hypotension and eventual CA. During Phase III (hyperemia), immediately following CPR, a rapid increase in CBF and oxygenation occurred. During Phase IV (hypoperfusion), CBF stabilized at a level below baseline, but oxygen extraction increased, leading to a decrease in brain oxygenation.

Temporal Dynamics of Cerebral Perfusion and Metabolism in CA/CPR Model

Figure 2:
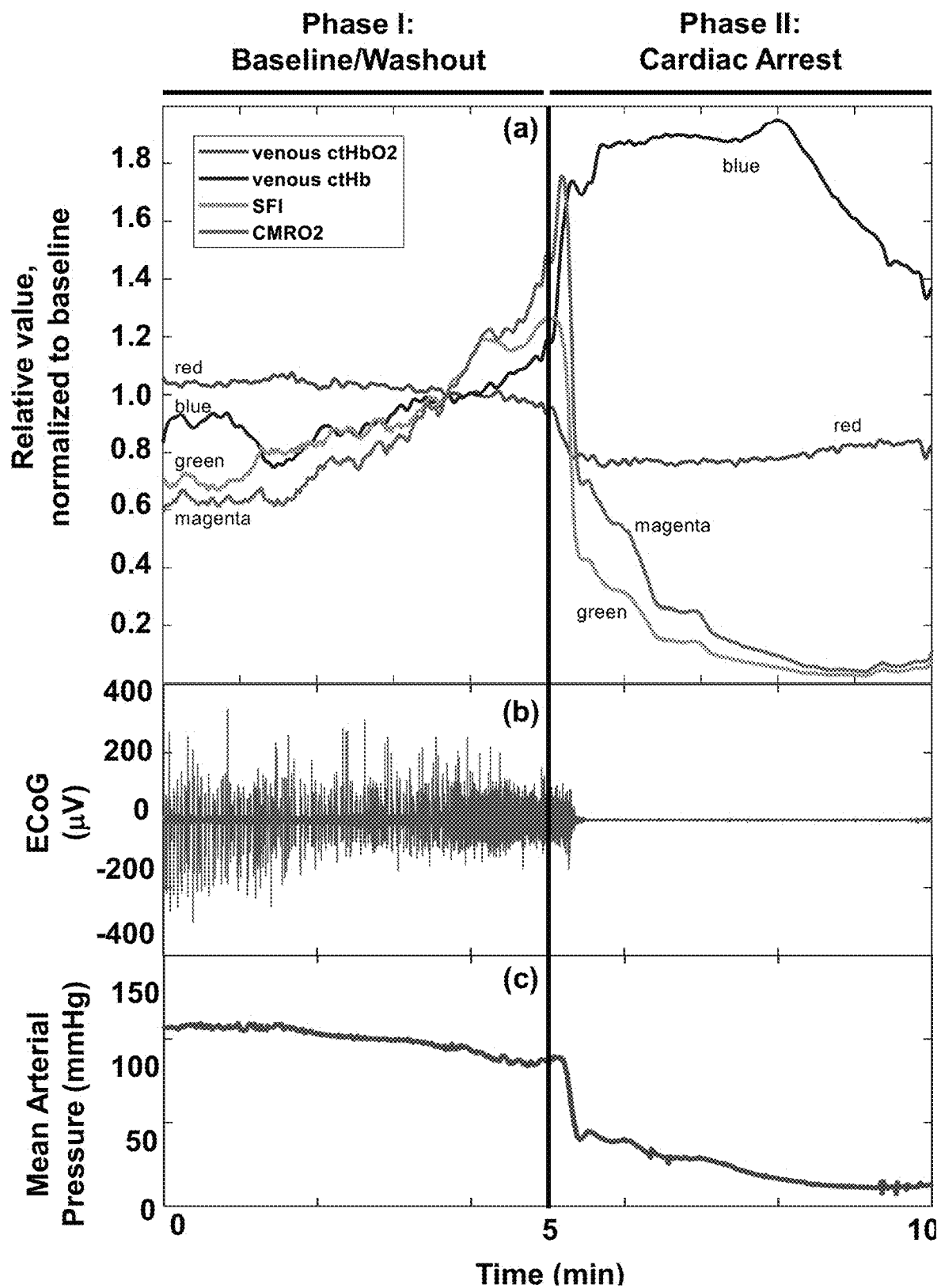
Figure 3:
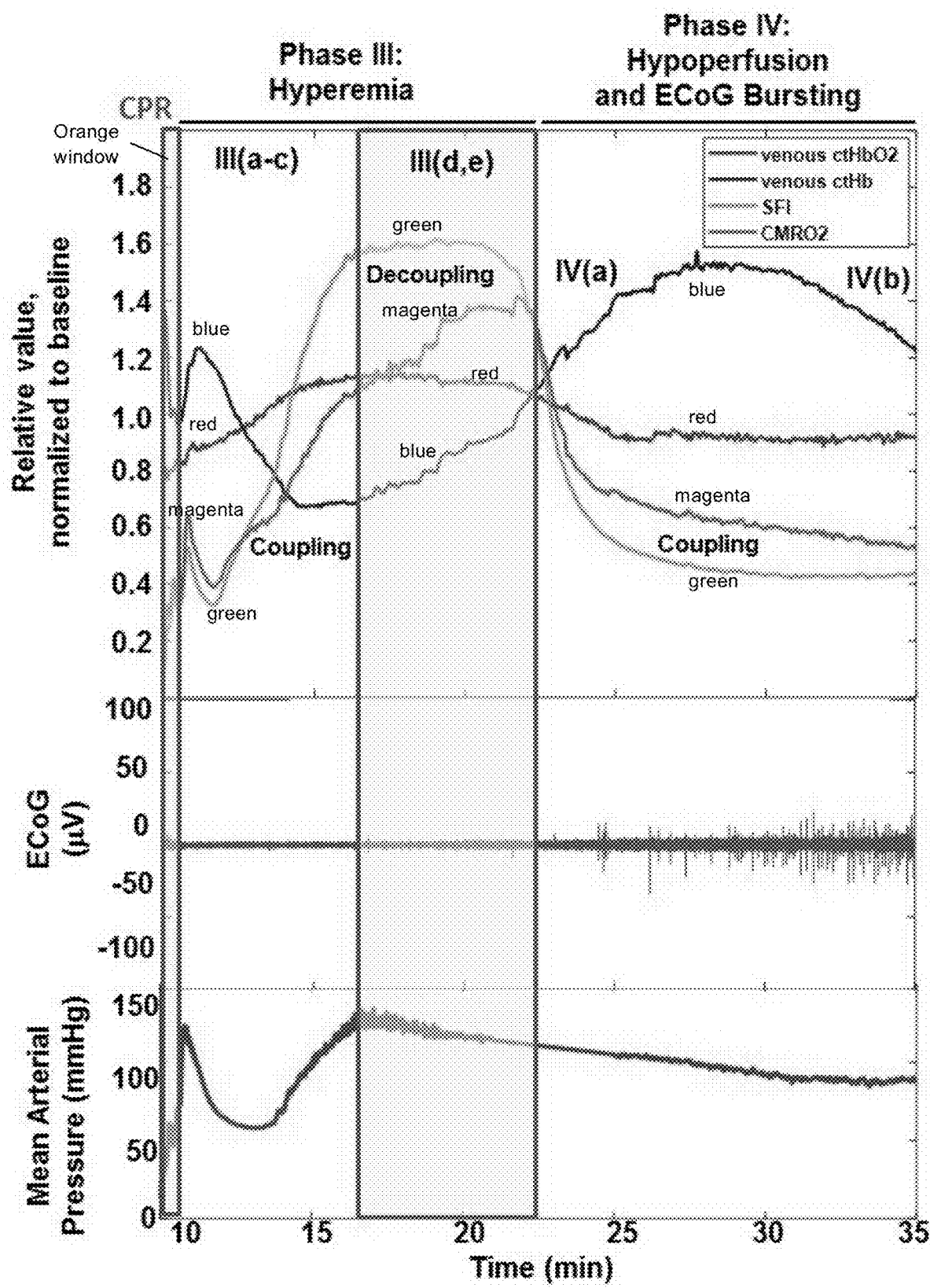

FIGS. 2-3 illustrate the dynamic relationship between CBF and CMRO$_2$ in a representative rat. As shown in FIG. 2 (a) and (b), during Phase I, CBF (green), deoxy-hemoglobin (blue), CMRO$_2$ (magenta), and ECoG activity all increased during isoflurane washout. During Phase II, ECoG showed electrocerebral silence within ~30 sec following onset of asphyxia concomitantly with a decrease in systemic blood pressure (c). Also, during Phase II, a large decrease in CBF, oxy-hemoglobin (red), and CMRO$_2$ was observed with a large (~50%) increase in deoxy-hemoglobin, as oxygen extraction occurred in the absence of perfusion. As shown in FIG. 3, during Phase III, ROSC was associated with a hyperemic state, yet electrocerebral silence persisted. During Phase IV, CBF decreased to a stabilized level, deoxy-hemoglobin increased, and ECoG activity resumed. These Phase IV dynamics signified increased oxygen extraction relative to perfusion, coinciding with increased neuronal activity.

Five sub-phases were identified during Phase III (FIG. 3). During Phase III(a), which lasted for only ~1 min post-CPR, a transient increase in deoxy-hemoglobin, followed immediately by a transient decrease in CBF and CMRO$_2$, was observed. During Phase III(b), CBF, oxy-hemoglobin, and CMRO$_2$ increased and deoxy-hemoglobin decreased. During Phase III(c), CMRO$_2$ and CBF continued to increase, but oxy-hemoglobin reached a plateau and deoxy-hemoglobin began to increase, in a manner similar to that seen in Phase I. During Phase III(d), CMRO$_2$ and deoxy-hemoglobin continued to increase, but oxy-hemoglobin slightly decreased while CBF reached a plateau. During Phase III(e), a noticeable transient decoupling between flow and metabolism was observed, as CMRO$_2$ reached a plateau while CBF decreased sharply. This decoupling phase immediately preceded the initial ECoG burst. 6 of the 10 rats exhibited either a period like Phase III(e) or a period where CMRO$_2$ increased only slightly during Phase III(c) while CBF was changing rapidly.

Phase IV contains two main sub-phases. During Phase IV(a), CBF and CMRO$_2$ decrease sharply, oxy-hemoglobin continues to decrease gradually, and deoxy-hemoglobin increases. During Phase IV(b), CBF has stabilized at a level below pre-CA baseline and deoxy-hemoglobin gradually reaches a steady value. The end of hyperemia coincides with initial ECoG bursting and the transition between Phases III and IV, marked by the intersection of the CBF and CMRO$_2$ curves. Following initial burst, ECoG recovery occurs, likely causing increased cerebral oxygen extraction that can cause the increase in deoxy-hemoglobin. This critical period of transition between Phases III and IV is evident from the combination of the CBF and oxygenation data but cannot be determined from the mean arterial pressure.

Figure 4A:
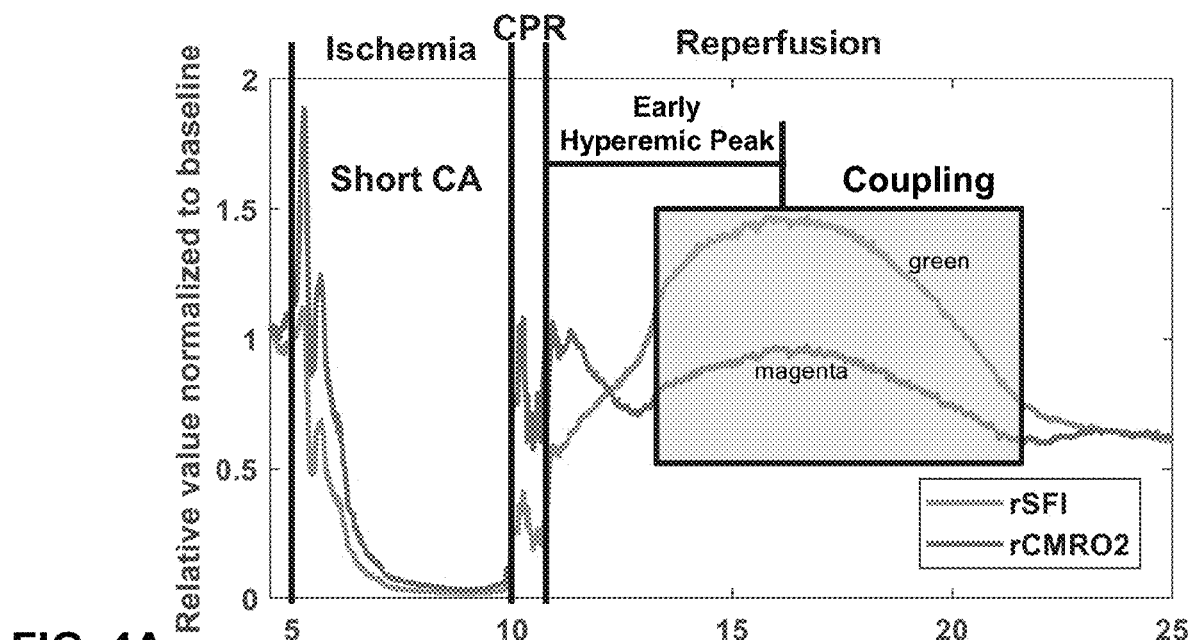
FIG. 4A shows CBF and $CMRO_2$ for a representative rat with short CA (5 min asphyxia) having an early, temporally-synchronous (coupled) recovery of CBF and $CMRO_2$ in the post-ROSC period.
Figure 4B:
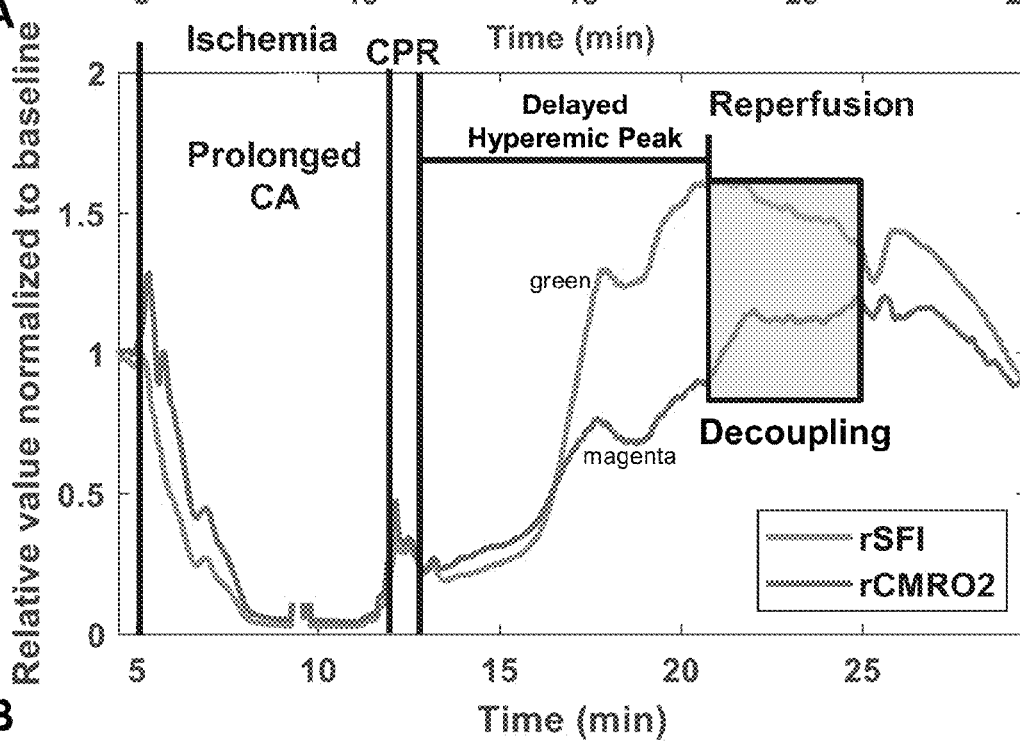
FIG. 4B shows CBF and $CMRO_2$ for a representative rat with prolonged CA (7 min asphyxia) having a delayed recovery of CBF and $CMRO_2$ in the post-ROSC period with periods of decoupling between CBF and $CMRO_2$ temporal dynamics (shaded box).
Figure 4C:
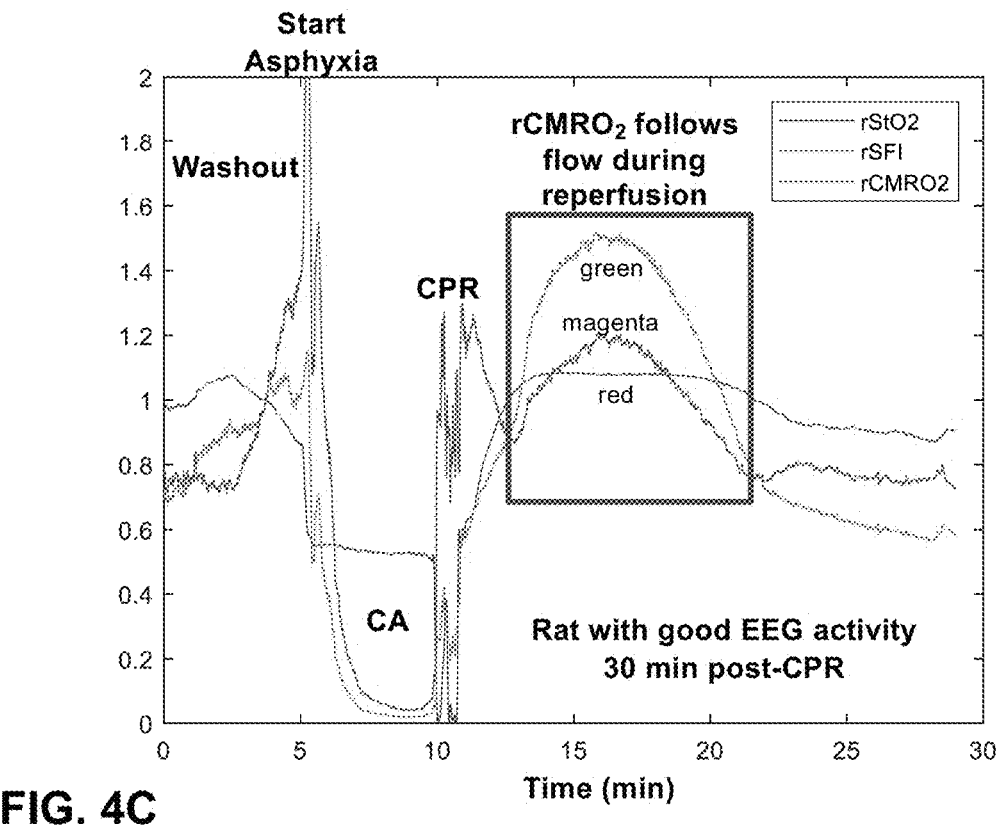
FIG. 4C shows $StO_2$, SFI, and $CMRO_2$ for a representative rat with good EEG activity 30 min post-CPR, where $CMRO_2$ follows flow during reperfusion (box).
Figure 4D:
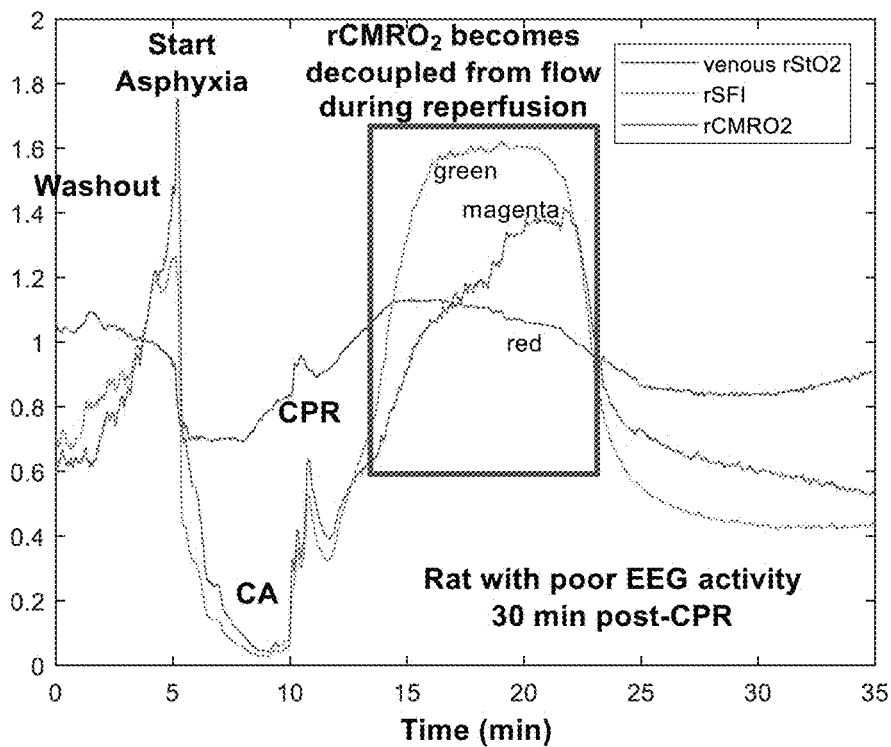
FIG. 4D shows $StO_2$, SFI, and $CMRO_2$ for a representative rat with poor EEG activity 30 min post-CPR, where $CMRO_2$ becomes decoupled from flow during reperfusion (box).

Flow-Metabolism Coupling and Uncoupling Post-CPR May be Influenced by CA Duration FIGS. 4A and 4B show CBF and CMRO$_2$ for two representative rats: one with a 5 min asphyxial period and earlier time to initial ECoG burst frequency (4A), and one with a 7 min asphyxial period and delayed recovery of burst frequency (4B). For the rat with the shorter CA and earlier ECoG bursting, the CBF and CMRO$_2$ dynamics are coupled throughout the reperfusion period. This similarity in the CBF and CMRO$_2$ lineshapes, with the magnitude of the CBF change exceeding the magnitude of the CMRO$_2$ change, is similar to that observed in stimulus-evoked CBF and CMRO$_2$ measurements in healthy subjects. For the rat with the longer CA and delayed ECoG bursting, a longer time period occurred prior to recovery of CBF and CMRO$_2$, and the flow-metabolism dynamics were less coupled during hyperemia. Specifically, toward the middle of the hyperemic period (shaded box), CBF and CMRO$_2$ trended in opposite directions, suggesting a mismatch between periods of increased blood flow and periods of greater metabolic demand in this rat. In four of the five rats with prolonged (7 min) asphyxia, notable differences were observed between the rate of change of CBF and the rate of change of CMRO$_2$ during the reperfusion period. These periods of uncoupling were only seen in two of the five rats with shorter (5 min) asphyxia.

Flow-Metabolism Mismatch in the Brain Within the First Minute Post-CPR Can Assess CA Duration and Predict Cerebral Electrical Recovery Next, the flow/metabolism mismatch can be measured by calculating the ratio of CBF and CMRO$_2$. FIG. 5A shows the CBF/CMRO$_2$ ratio during the first minute after resuscitation for 5 rats with shorter CA (5 min asphyxia; solid lines) and 5 rats with prolonged CA (7 min asphyxia; dashed lines). This figure shows that a threshold can be placed on the value of CBF/CMRO$_2$ in the window of ~0.5-1 min post-resuscitation (vertical line at CBF/CMRO$_2$~1 in FIG. 5B) to separate the rats with shorter CA from the rats with prolonged CA. This result suggests, that within 1 min of resuscitation, the CBF/CMRO$_2$ ratio can be used for assessment of the severity (duration) of CA, without any prior knowledge of the cardiac or hemodynamic history of the patient. This threshold makes sense physically, because CBF/CMRO$_2$<1 can be thought of as a marker of flow-metabolism mismatch (i.e. CBF is insufficient to meet metabolic demand). The CA severity assessment capability of the CBF/CMRO$_2$ ratio vanished within 3 min of ROSC.

Furthermore, a second threshold can be placed at CBF/CMRO$_2$~1.2 to differentiate between rats with poor short-term recovery (longer time to ECoG bursting) and those with good short-term recovery (shorter time to ECoG burst), independent of CA duration. FIG. 5B shows a scatter plot for the values of this ratio for all rats, plotted against the time to initial ECoG burst. The relationship between CBF/CMRO$_2$ and initial ECoG burst was statistically significant using a Pearson correlation (r=−0.74, p=0.014) and a Spearman correlation (r=−0.67, p=0.039). Overall, a higher flow/metabolism index immediately after ROSC is associated with a shorter asphyxial CA period and a better neurological outcome as measured by faster ECoG bursting. The ECoG burst time prediction capability of the CBF/CMRO$_2$ ratio also vanished within 3 min of ROSC.

To test the prognostic ability of the CBF/CMRO$_2$ ratio, a predictive model was created by performing leave-one-out cross-validation with linear fits to the points on the scatter plot of ECoG burst time vs. CBF/CMRO$_2$ at 1 min post-ROSC. Using this technique, the CBF/CMRO$_2$ ratio was predictive of the initial burst time with 87% accuracy. Importantly, the CBF/CMRO$_2$ mismatch ratio provided both CA severity assessment and recovery prognosis simultaneously at an ultra-early time point (~0.5-2 min post-ROSC).

To further analyze the impact of flow-metabolism mismatch immediately post-ROSC on early neurological recovery, additional indices related to the difference between CBF and CMRO$_2$ were calculated and compared to the time of the first EEG burst post-ROSC. FIGS. 6A and 6B show CBF and CMRO$_2$, normalized to the corresponding value at 15 sec post-ROSC, for the first 5 min post-ROSC for representative rats with shorter CA (6A) and longer CA (6B). During this time period, the relative CBF is higher than the relative CMRO$_2$ for the rat with shorter CA, but the relative CMRO$_2$ is higher than the relative CBF for the rat with the prolonged CA. This suggests that greater CBF in comparison to metabolic demand by the brain is associated with shorter CA duration. FIG. 6C shows that the ratio of the areas under the CBF and CMRO$_2$ curves from 0.25-3 min post-ROSC was statistically significant for distinguishing between shorter CA and prolonged CA.

Rate of Change of CBF in the First Minute Post-ROSC Correlates with Time to Resumption of Cerebral Electrical Activity FIG. 7 shows that CBF alone, measured within the first minute post-ROSC and normalized to its value at 15 sec post-ROSC, can be employed to predict time of initial ECoG burst. A linear regression (black line; R=−0.77, p=0.01 from Pearson correlation) was fit to the data, thus providing a statistically-significant correlation. Using a leave-one-out cross-validation technique, this metric predicted first ECoG burst to within 16% over the entire cohort of rats, including both shorter and prolonged asphyxia times. This result suggests that the lower the CBF after completion of CPR, the longer it will take for the brain's electrical activity to resume. This result suggests that knowledge of the total time-integrated perfusion is not required to predict ECoG bursting; only the change in CBF 30 sec post-ROSC relative to its value at 15 sec post-ROSC is required.

Discussion

Impaired Autonomic Regulation in Acute Brain Injury Motivates Use of Flow-Metabolism Metrics In the healthy brain, autonomic regulation is intact, so a neural stimulus will trigger an appropriate increase in CBF, matched with the corresponding increase in metabolic demand. Typically, the CBF response will overshoot the increase in metabolism; this is a normal physiological reaction designed to maintain a reserve supply of oxygen in case metabolic demand increases or the ambient oxygen level decreases. This type of system is a classic example of optimal neurovascular coupling and intact autonomic regulation. However, after acute cerebral ischemia or other forms of brain trauma, cerebral autonomic regulation may be compromised, causing impaired neurovascular coupling and mismatches between CBF and metabolism. Therefore, it is critical to obtain better quantitative understanding of flow-metabolism mismatch immediately following these types of insults because CBF, blood pressure, oxygenation, or cortical electrical activity alone may not provide an accurate picture of brain function and neural dynamics during these critical time periods.

The present invention has found that deviations of the CBF/CMRO$_2$ ratio from unity within the first minute post-ROSC can assess CA severity (asphyxia duration) and predict cerebral electrical recovery (time to first ECoG burst). The CBF/CMRO$_2$ ratio at 1 min post-ROSC is predictive of ECoG burst time with 87% accuracy (Table 1). Interestingly, these correlations do not persist at later time points, suggesting that the first 1-3 minutes post-ROSC may provide a critical but transient window during which to perform therapeutic maneuvers to improve neurological outcome after CA.

TABLE 1

The ratio between CBF and CMRO$_2$ (CBF/CMRO$_2$; column 2) 1 min post-ROSC can be input into a linear regression model to predict time to initial ECoG burst (TTB). Using a leave-one-out cross-validation technique, the mean percent error for predicting TTB was 13% over the full cohort of rats in this experiment, and the error did not exceed 21% for any of the rats. Prior to this calculation, CBF and CMRO$_2$ were normalized to their respective values at 15 sec post-ROSC. The method did not require any pre-ROSC information.

| Ischemia Duration (min) | CBF/CMRO$_2$ at 1 min post-ROSC | Predicted TTB (min post-ROSC) | Detected TTB (min post-ROSC) | % Error |
| --- | --- | --- | --- | --- |
| 5 | 1.40 | 11.0 | 12.3 | 10.5% |
| 5 | 1.11 | 13.4 | 16.7 | 19.9% |
| 5 | 1.25 | 12.8 | 11.5 | 11.3% |
| 5 | 1.54 | 11.3 | 9.4 | 20.9% |
| 5 | 1.01 | 14.4 | 15.5 | 7.1% |
| 7 | 0.92 | 15.3 | 14.5 | 5.4% |
| 7 | 0.94 | 15.4 | 13.4 | 14.8% |
| 7 | 0.92 | 15.4 | 13.8 | 11.9% |
| 7 | 0.86 | 15.1 | 18.0 | 16.3% |
| 7 | 0.90 | 15.7 | 14.0 | 12.3% |

Immediate Flow-Metabolism Monitoring is Critical for Improving CA Patient Outcome Post-CPR CA patients typically suffer pronounced and prolonged brain damage due to cerebral ischemia. For patients who undergo out-of-hospital CA, 68% of fatalities are attributed primarily to ischemia-related brain injury, and fewer than 9% survive with "Good or Moderate Cerebral Performance" (defined as Cerebral Performance Category 1 or 2). Currently, there are no widely-accepted clinical treatments to improve CA patient outcome (with the exception of targeted temperature management), and developing prognostic tools to optimize blood pressure, oxygen, and carbon dioxide levels for these patients is an active area of investigation. Recently, it has been suggested that increasing the mean arterial pressure immediately post-ROSC can mitigate flow-metabolism uncoupling by maximizing CBF. However, it is also known that too high of a CBF or oxygenation level during this critical period can potentially increase the risk of reperfusion injury and oxidative damage to mitochondria and neurons. Therefore, there is an unmet clinical need for real-time quantitative monitoring of CBF and brain metabolism following CA, especially in the transient hyper-dynamic period immediately post-CPR. In the intensive care setting, brain function of CA patients is typically monitored with electroencephalography (EEG), and perfusion is usually assessed via peripheral blood pressure. As a result, the underlying mechanisms driving recovery of cerebral electrical activity following hypoxic-ischemic injury are not well-characterized, and measuring them could lead to improvements in patient care.

Cerebral Perfusion/Metabolism Mismatch Can Predict Ischemic Injury or Perfusion Damage to Prognosticate Neurological Recovery and Inform Treatment An optimal CBF range to promote cerebral recovery following ischemic injury, such as CA, is defined not by the CBF alone, but by the amount of perfusion relative to cerebral metabolism. Determining this optimal balance of flow-metabolism matching to allow optimal neurovascular coupling is especially critical during periods of cerebral autonomic dysregulation, which occurs after acute brain injury (including ischemic injury and traumatic brain injury). Therefore, measuring CBF and $CMRO_2$ in tandem is crucial, and the $CBF/CMRO_2$ ratio may be used to indicate ischemic damage ($CBF/CMRO_2 < 1$) or excess perfusion ($CBF/CMRO_2 \gg 1$).

Without wishing to limit the present invention to a particular theory or mechanism, it may be optimal to have a $CBF/CMRO_2$ ratio that exceeds 1 in the first few minutes post-CPR; this ratio may need to be much greater than 1 to indicate perfusion injury. By contrast, at 1 min post-ROSC, a $CBF/CMRO_2$ ratio that is even slightly below 1 (or, in fact, slightly above 1) may indicate risk of ischemic injury, as animals with delayed ECoG bursting had $CBF/CMRO_2 < 1.2$ at this early time point. The significant prognostic metrics in this experiment were all found at time points within ~3 min post-ROSC. After that time window ended, these metrics lost their prognostic significance. The transient nature of this prognostic window may be a potential explanation for why it is currently difficult for clinicians to determine the optimal blood pressure for post-CA patients in the intensive care unit. Specifically, peripheral blood pressure may be decoupled from CBF, measurements of CBF are not typically combined with cerebral oximetry, and there is often a significant time delay between ROSC and measurements of cerebral perfusion. Continuously monitoring CBF and $CMRO_2$ immediately post-ROSC may provide real-time feedback to clinicians to optimize treatment and improve cerebral recovery for CA patients.

Measuring Flow-Metabolism Mismatch Can Provide Early Assessment of CA Severity/Duration In addition to prognosis of cerebral electrical recovery, the $CBF/CMRO_2$ ratio at 1 min post-ROSC provided complete distinction between rats that had undergone mild CA (5 min asphyxia) and rats that experienced more severe CA (7 min asphyxia). Specifically, rats that experienced more severe CA had lower $CBF/CMRO_2$ ratios (suggesting ischemic injury) at this time point than rats with milder CA. Therefore, quantifying the flow-metabolism mismatch can also potentially assess severity/duration of ischemia. Obtaining this assessment would be transformational in clinical management and prognostication of post-CA patients because true "down-time" (hypoxic-ischemic duration) is often not known when first responders arrive on the scene. Furthermore, for the two rats that underwent mild CA but recovered poorly (one experiencing significant blood loss, one exhibiting a delayed initial ECoG burst), the $CBF/CMRO_2$ ratio was closer to those of the animals with more severe CA. This result suggests that quantifying cerebral perfusion-metabolism mismatch can potentially provide finer stratification of CA severity assessment and recovery prognosis across multiple subgroups of CA/CPR patients.

In conclusion, the present invention has quantified the highly-dynamic relationship between CBF and brain metabolism ($CMRO_2$) in a preclinical model of CA and CPR. Different degrees of coupling between CBF and $CMRO_2$ were observed in different temporal windows over the first ~20 min following CPR and the degree of flow-metabolism mismatch was calculated by using the metric $CBF/CMRO_2$. This mismatch was significant for assessing CA severity (distinguishing shorter, less severe CA from more prolonged CA) and prognostically significant (correlating with time to initial ECoG burst) within the first minute post-ROSC. However, the statistical significance of these correlations vanishes within ~3 min post-ROSC, suggesting the presence of a transient, critical time window during which continuous monitoring of CBF and $CMRO_2$ may be crucial for optimizing treatment for CA patients.

Furthermore, the present invention may be of great potential importance in a clinical scenario where a CA patient presents to first responders, emergency medicine physicians, or intensive care physicians who may lack knowledge of the exact time when CA occurred prior to achieving return of spontaneous circulation (ROSC). Since the perfusion and metabolism metrics reported here only require knowledge of CBF and $CMRO_2$ in the first minute post-CPR, these metrics can help inform urgent clinical decision making in the critical period immediately post-CPR.

EXAMPLE 2

The following is a non-limiting example of the present invention. It is to be understood that said example is not intended to limit the present invention in any way. Equivalents or substitutes are within the scope of the present invention.

Introduction

There is a significant clinical need for quantitative methods to measure cerebral metabolism in vivo to assess damage and recovery in brain-injured patients. Current techniques for quantifying brain metabolism are typically expensive, bulky, and unable to provide high temporal resolution. Diffuse optical spectroscopy and imaging have the potential to rapidly and portably monitor cerebral blood flow (CBF) and brain oxygenation ($StO_2$) simultaneously. Combining these measurements can quantify the cerebral metabolic rate of oxygen ($CMRO_2$) to measure brain metabolism on an absolute physiological scale (units of µM $O_2$ consumed/min) without the need for physiological perturbations (e.g., gas challenges). The present example introduces a new approach to quantify $CMRO_2$ in rats using multimodal diffuse optical technology.

Materials and Methods

Laser Speckle Imaging (LSI), using an 809 nm laser and a CCD camera, was employed to obtain Speckle Flow Index (SFI), a surrogate measure of CBF, in the rat brain. Concomitantly, brain absorption and reduced scattering coefficients ($\mu_a$, $\mu_s'$) were obtained using Spatial Frequency Domain Imaging (SFDI) at 655 nm, 730 nm, and 850 nm. The wavelength-dependent $\mu_a$ was analyzed to obtain concentrations (µM) of oxygenated and deoxygenated hemoglobin in the brain tissue ($ctHbO_2$ and ctHb, respectively). The values of $\mu_a$ and $\mu_s'$ were input into a correlation diffusion model to correct the SFI for absorption and static scattering, providing a quantitative map of the cerebral Brownian diffusion coefficient $D_B$ ($mm^2$/sec). The extracted values of $D_B$, ctHb, and the mean penetration depth of light in the tissue (also modeled with diffusion theory) were combined to form an empirical equation for $CMRO_2$ in units of µM $O_2$ consumed/min. The mean baseline values of $CMRO_2$ obtained with this method for 10 male Wistar rats (in accordance with IACUC guidelines) under isoflurane anesthesia were compared with those obtained from a previously-developed method that required induction of a "zero-flow" perturbation where the blood flow to the brain was temporarily stopped.

Results and Discussion

As seen in FIG. 8, a significant correlation was observed between the $CMRO_2$ values measured with the method described in this study and those measured with the "zero-flow" method described previously (r=0.72, p=0.018 from Pearson correlation). These results suggest that this technique is capable of quantifying cerebral oxygen metabolism without need for introducing a significant perturbation to the physiological system being measured.

Conclusions

The present example features a multimodal diffuse optical technique to rapidly measure cerebral metabolic rate of oxygen ($CMRO_2$) in quantitative physiological units (µM $O_2$ consumed per minute) without needing to induce a physiological perturbation. The technique was validated in a preclinical rat model and may be translatable for clinically-compatible measurements. The technique may allow for characterization of baseline $CMRO_2$ values to enable subject-to-subject comparison and longitudinal comparison without requiring dynamic experiments (e.g., gas challenges).

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

What is claimed is:

1. A method of determining brain damage severity and prognosing recovery after an ischemic and reperfusion event in a subject, said method comprising:
    a. illuminating a target tissue of the subject using one or more light sources of a diffuse optical measurement system to enable direct or surrogate measures of flow or pressure;
    b. detecting remitted light from the target tissue using a first detector of the system and recording measurements of the remitted light;
    c. projecting spatial frequency patterns of light onto the target tissue using a spatial light modulator coupled to a plurality of light emitting diodes (LEDs) of a spatial frequency domain imaging (SFDI) system, optically interrogating the tissue using diffuse optical spectroscopy (DOS), near-infrared spectroscopy (NIRS), frequency-domain photon migration DOS (FDPM-DOS), frequency-domain photon migration NIRS (FDPM-NIRS), time-resolved diffuse optical spectroscopy (TR-DOS) or time-resolved near-infrared spectroscopy (TR-NIRS) system, or any combination of these technologies, using one or more wavelengths in the visible, near-infrared, or short-wave infrared region;
    e. calculating speckle flow index (SFI) values, blood flow index (BFI), Brownian diffusion coefficient (Db), directed flow speed (vc), or another direct or surrogate measure of flow or pressure using the diffuse optical measurements, wherein the SFI, BFI, Db, or vc values are measurements of cerebral blood flow (CBF);
    f. determining deoxyhemoglobin and hemoglobin concentrations from measurements from any of the systems described in (c);
    g. calculating a relative cerebral metabolic rate of oxygen ($CMRO_2$) using CBF measurements and deoxyhemoglobin and hemoglobin concentrations; and
    h. calculating a ratio of the CBF to $CMRO_2$;
    wherein within a specific period of time after resuscitating the subject, the CBF:$CMRO_2$ ratio can provide a severity assessment and recovery prognosis for the subject, wherein the CBF:$CMRO_2$ ratio quantifies a degree of mismatch between cerebral perfusion and metabolism, and serves as a metric of cerebral autoregulation, wherein if the CBF:$CMRO_2$ ratio is at or below a threshold, the ratio is indicative of ischemic damage, wherein if the CBF:$CMRO_2$ ratio is above a higher threshold, the ratio is indicative of excess perfusion.

2. The method of claim 1, wherein the specific period of time is less than 10 minutes.

3. The method of claim 1, wherein the specific period of time is about 10-300 seconds.

4. The method of claim 1, wherein the threshold is greater than or equal to 1.

5. The method of claim 1, wherein the ischemic event is cerebral ischemia caused by cardiac arrest, stroke, delayed cerebral ischemia after subarachnoid hemorrhage, or traumatic brain injury.

6. A system for determining brain damage severity and prognosing recovery after an ischemic event in a subject, said system comprising:
   a. a means for measuring cerebral blood flow (CBF);
   b. a means for measuring a relative cerebral metabolic rate of oxygen; and
   c. a processing unit comprising a memory and a processor operatively coupled to the memory, wherein the memory stores computer-readable instructions that when executed by the processor, causes the processor to perform operations comprising:
      i. determining the relative cerebral metabolic rate of oxygen ($CMRO_2$) using the measurements of CBF and cerebral oxygenation; and
      ii. calculating a ratio of the CBF to $CMRO_2$;
   wherein within a specific period of time after resuscitating the subject, the $CBF:CMRO_2$ ratio can be used to provide a severity assessment and recovery prognosis, wherein if the $CBF:CMRO_2$ ratio is at or below a threshold, the ratio is indicative of ischemic damage, wherein if the $CBF:CMRO_2$ ratio is above a higher threshold, the ratio is indicative of excess perfusion.

7. The system of claim 6 further comprising a means for measuring ECoG or EEG burst frequency for cerebral electrical activity, wherein the $CBF:CMRO_2$ ratio is predictive of ECOG burst time.

\* \* \* \* \*